(12) United States Patent
Kim

(10) Patent No.: US 12,370,283 B2
(45) Date of Patent: Jul. 29, 2025

(54) VEHICLE STERILIZING APPARATUS AND COCKPIT MODULE HAVING THE SAME

(71) Applicant: HYUNDAI MOBIS Co., Ltd., Seoul (KR)

(72) Inventor: Seung Cheol Kim, Yongin-si (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 753 days.

(21) Appl. No.: 17/692,524

(22) Filed: Mar. 11, 2022

(65) Prior Publication Data

US 2023/0201410 A1 Jun. 29, 2023

(30) Foreign Application Priority Data

Dec. 28, 2021 (KR) ........................ 10-2021-0189912

(51) Int. Cl.
*A61L 9/20* (2006.01)
*B64D 13/06* (2006.01)

(52) U.S. Cl.
CPC .............. *A61L 9/205* (2013.01); *B64D 13/06* (2013.01); *A61L 2209/14* (2013.01); *B64D 2013/0651* (2013.01)

(58) Field of Classification Search
CPC ..... A61L 9/00; A61L 9/18; A61L 9/20; A61L 9/205; A61L 2209/00; A61L 2209/01; A61L 2209/11; A61L 2209/111; A61L 2209/12; A61L 2209/14; A61L 2209/16; B60H 1/00; B60H 1/00507; B60H 1/00557; B60H 1/00564; B60H 3/00; B60H 3/0071; B60H 3/0078; B60H 3/06; B60H 3/0608; B60H 3/0658; B60H 2003/00; B60H 2003/06; B60H 2003/0675; B62D 25/00; B62D 25/08; B62D 25/14; B62D 25/142;
(Continued)

(56) References Cited

U.S. PATENT DOCUMENTS

| | | | |
|---|---|---|---|
| 2007/0222257 A1* | 9/2007 | Flendrig ................ | B60J 5/0447 296/146.6 |
| 2020/0061231 A1 | 2/2020 | Jeong et al. | |
| 2020/0254132 A1* | 8/2020 | Lee .......................... | B60H 1/34 |

FOREIGN PATENT DOCUMENTS

| | | |
|---|---|---|
| CN | 111359435 A | 7/2020 |
| CN | 214822496 U | 11/2021 |

(Continued)

OTHER PUBLICATIONS

Machine translation of KR 10-2031698 B1, provided with IDS filed on Dec. 14, 2022, which was published on Oct. 14, 2019 (Year: 2019).*

(Continued)

*Primary Examiner* — Natasha E Young
(74) *Attorney, Agent, or Firm* — MORGAN, LEWIS & BOCKIUS LLP

(57) ABSTRACT

A cockpit module according to an embodiment includes a speaker disposed on a crash pad, a cover disposed to cover the speaker, and a sterilizing apparatus disposed on the crash pad, in which a hole formed in the cover is disposed to face an inlet port and an outlet port of the sterilizing apparatus. Accordingly, the cockpit module may implement a sterilizing apparatus, which sterilizes and filters air in the cockpit module, to improve a degree of design freedom while improving vehicle interior hygiene.

16 Claims, 20 Drawing Sheets

(58) Field of Classification Search
CPC .................... B64D 13/00; B64D 13/06; B64D 2013/0603; B64D 2013/0651
See application file for complete search history.

(56) References Cited

FOREIGN PATENT DOCUMENTS

| | | |
|---|---|---|
| JP | H06-305325 A | 11/1994 |
| JP | H08-282383 A | 10/1996 |
| KR | 10-1152512 B1 | 6/2012 |
| KR | 10-2018-0129215 A | 12/2018 |
| KR | 10-1994906 B1 | 7/2019 |
| KR | 10-2031698 B1 | 10/2019 |
| KR | 10-2021-0064177 A | 6/2021 |
| KR | 10-2021-0094218 A | 7/2021 |

OTHER PUBLICATIONS

Office Action issued in corresponding Korean Patent Application No. 10-2021-0189912 dated Aug. 24, 2023.
Extended European Search Report issued in corresponding European Patent Application No. 22162423.2 dated Sep. 14, 2022.

* cited by examiner

[FIG. 1]
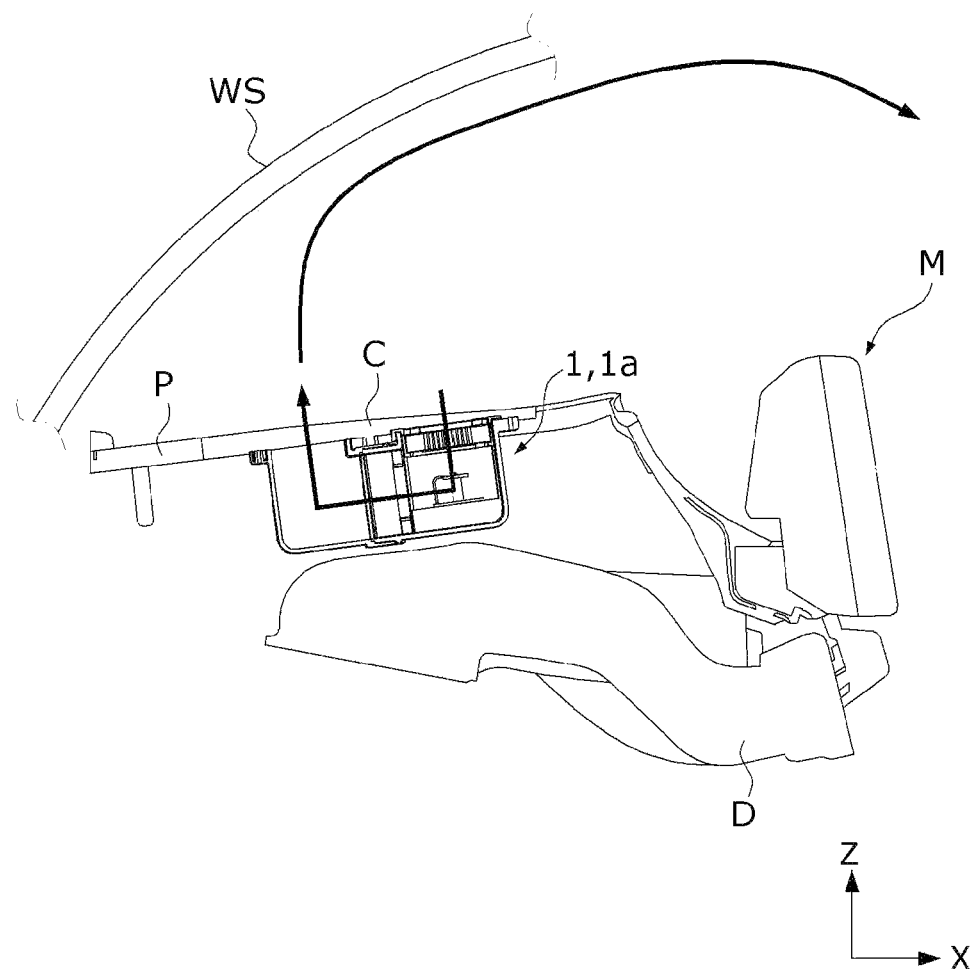

[FIG. 2A]
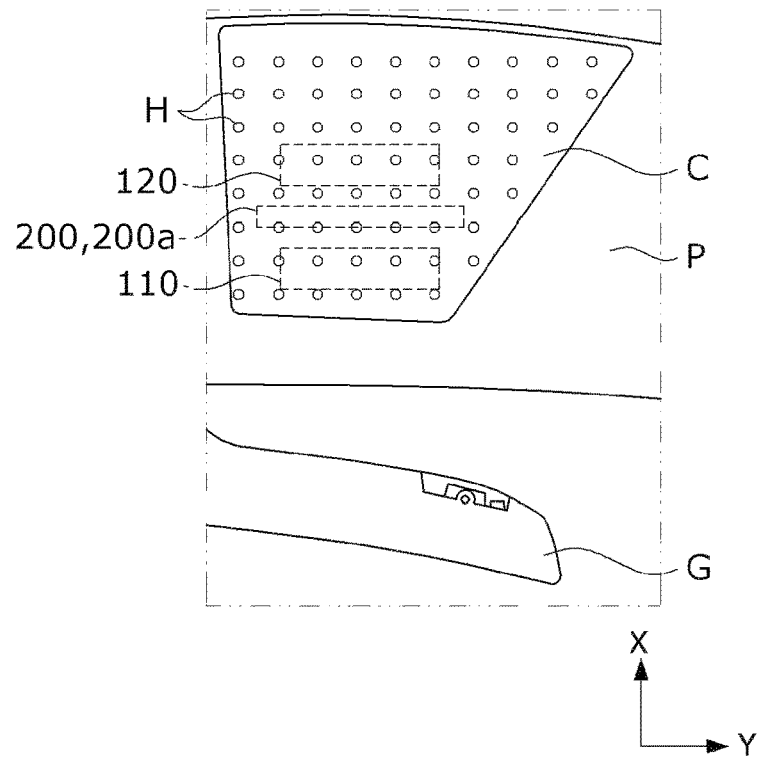
[FIG. 2B]
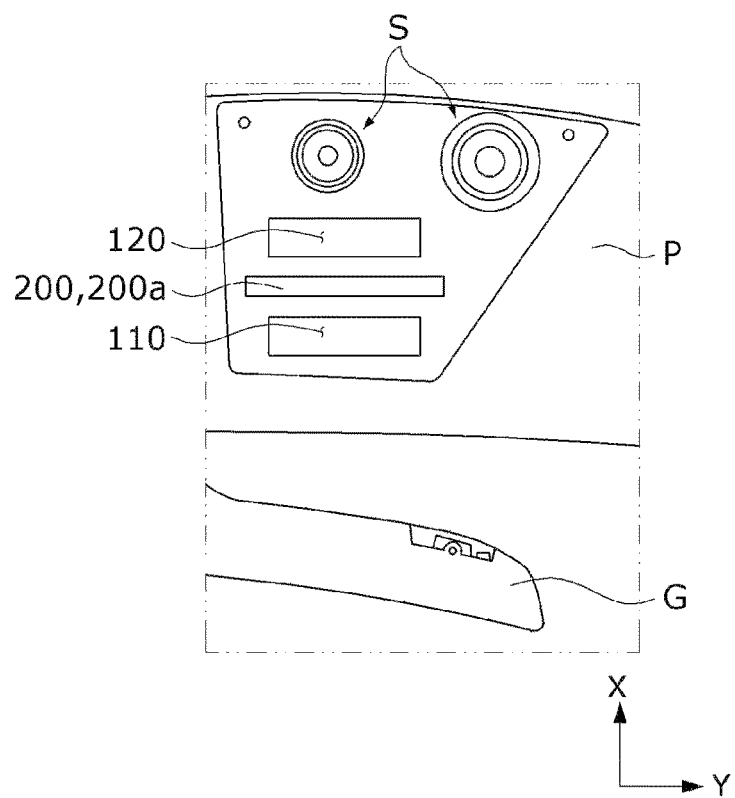

[FIG. 3]
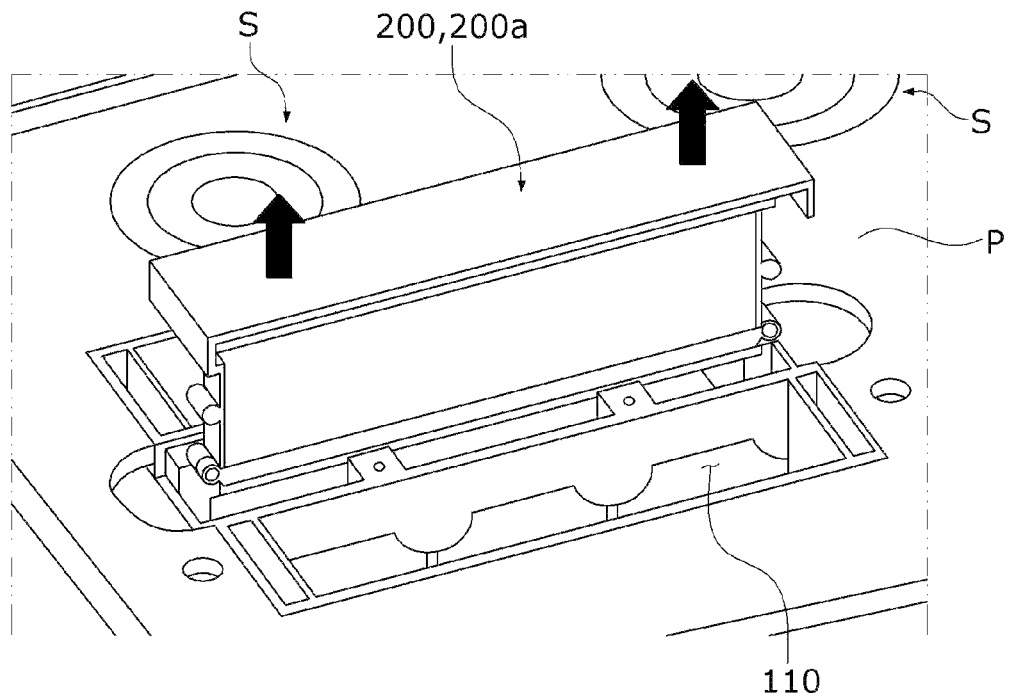
[FIG. 4]
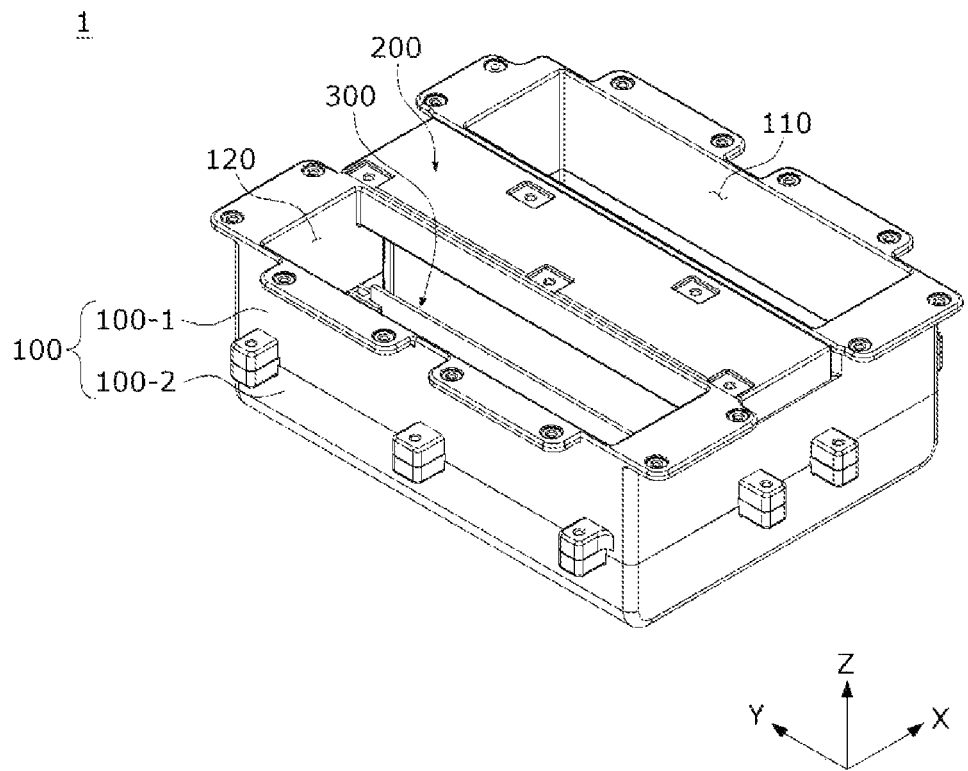

[FIG. 5]
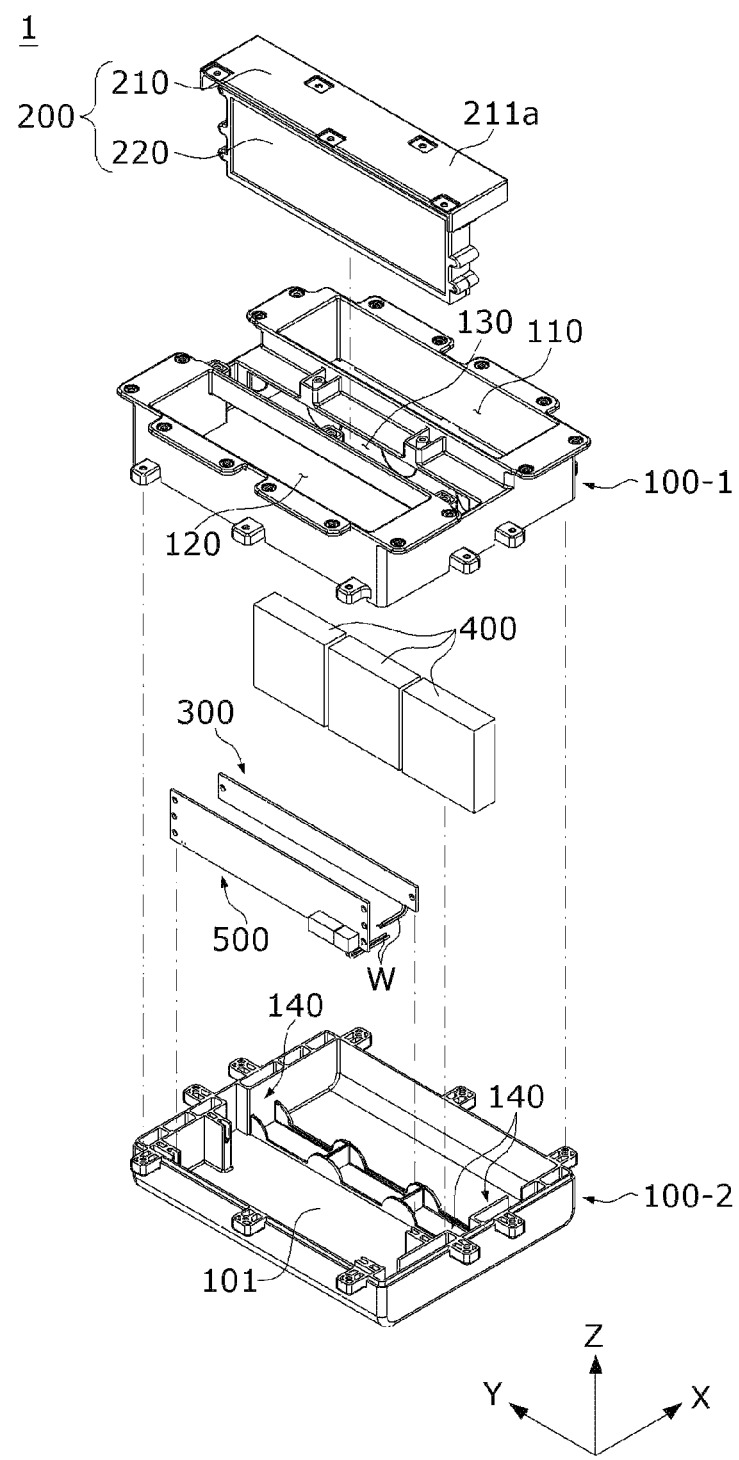

[FIG. 6]
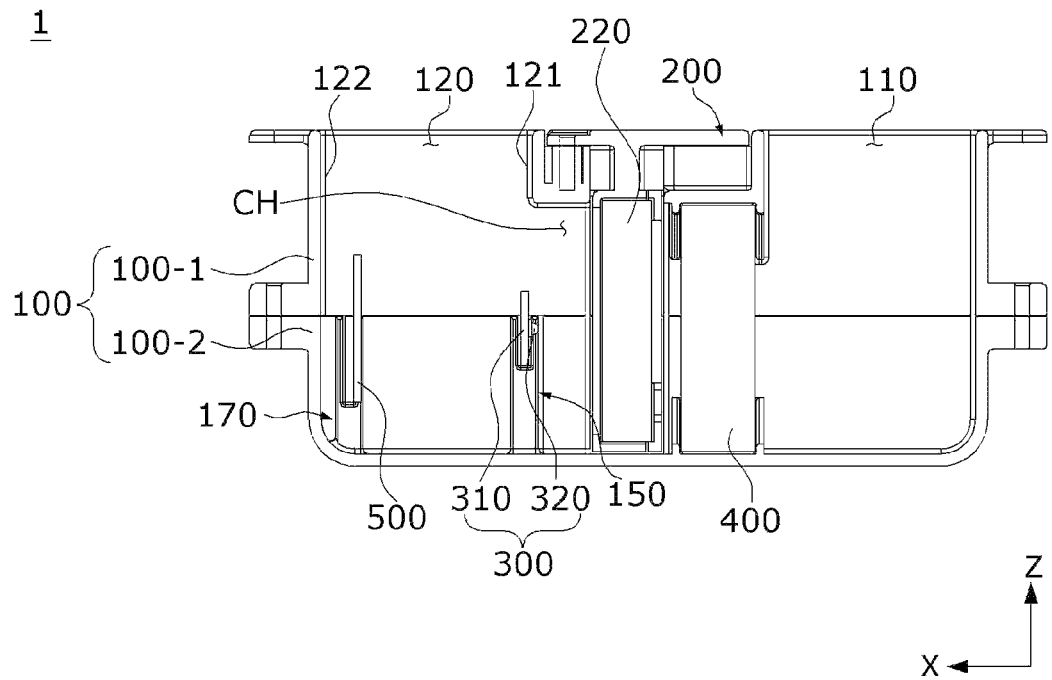
[FIG. 7]
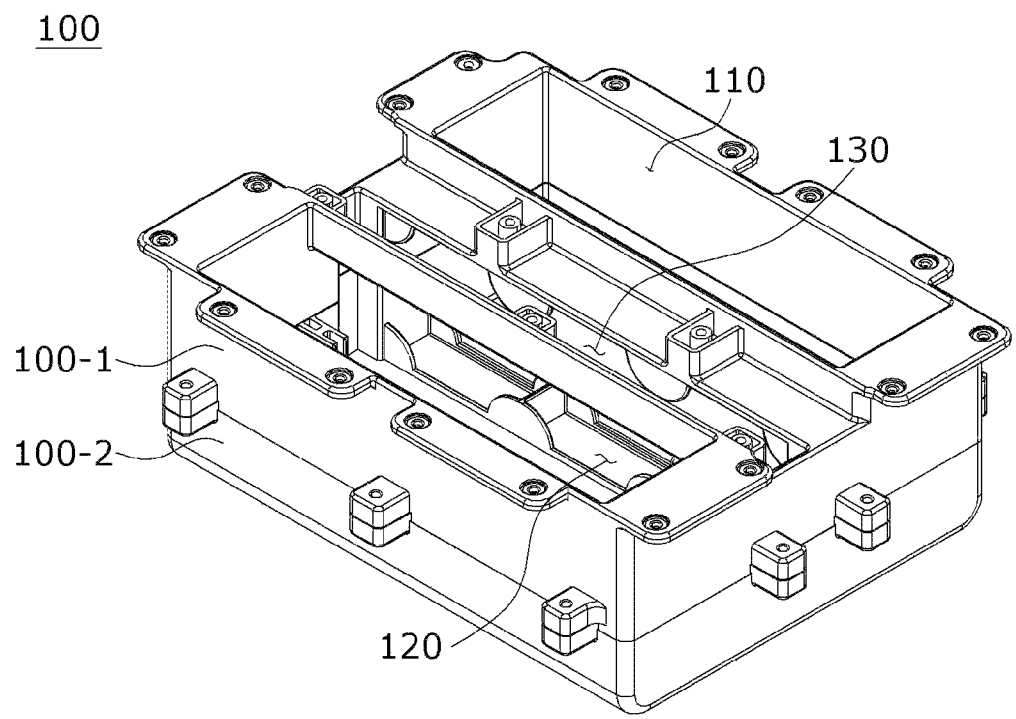

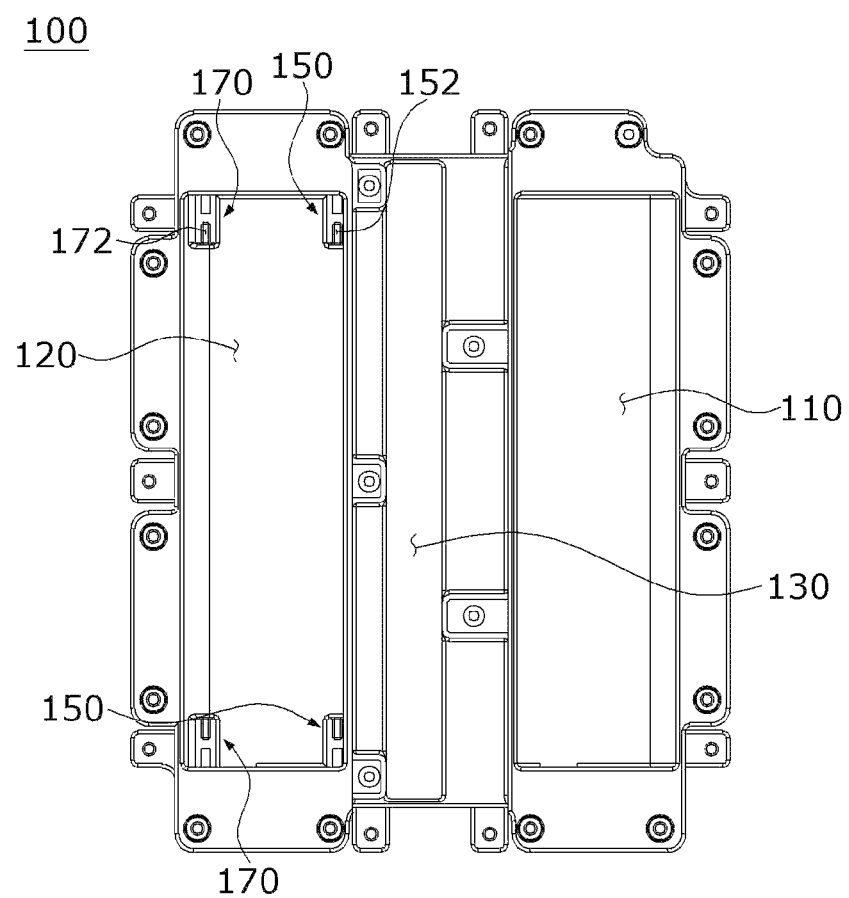
[FIG. 8]

[FIG. 9]
100-1
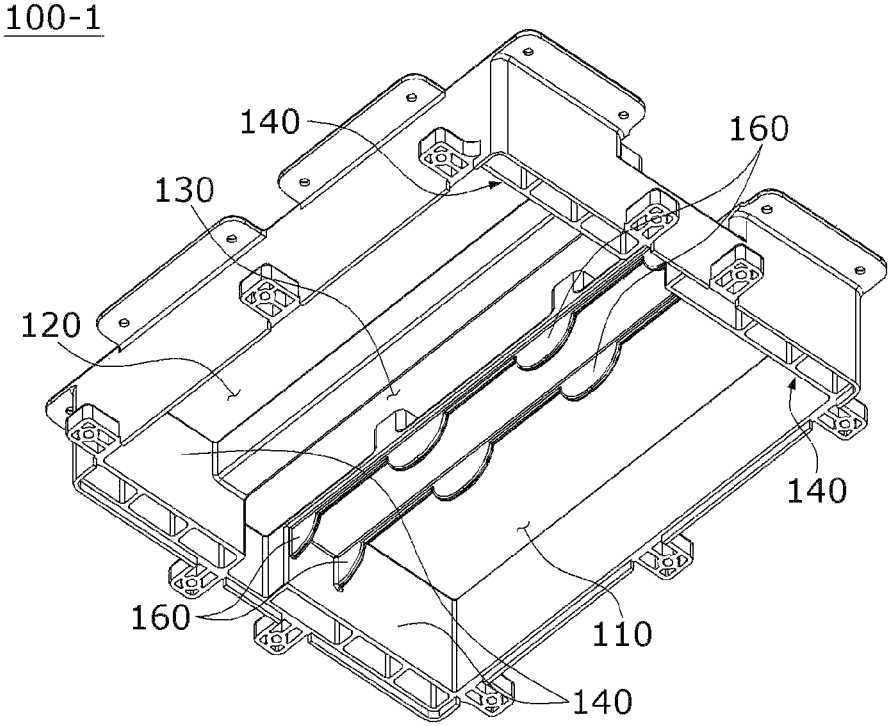

[FIG. 10]
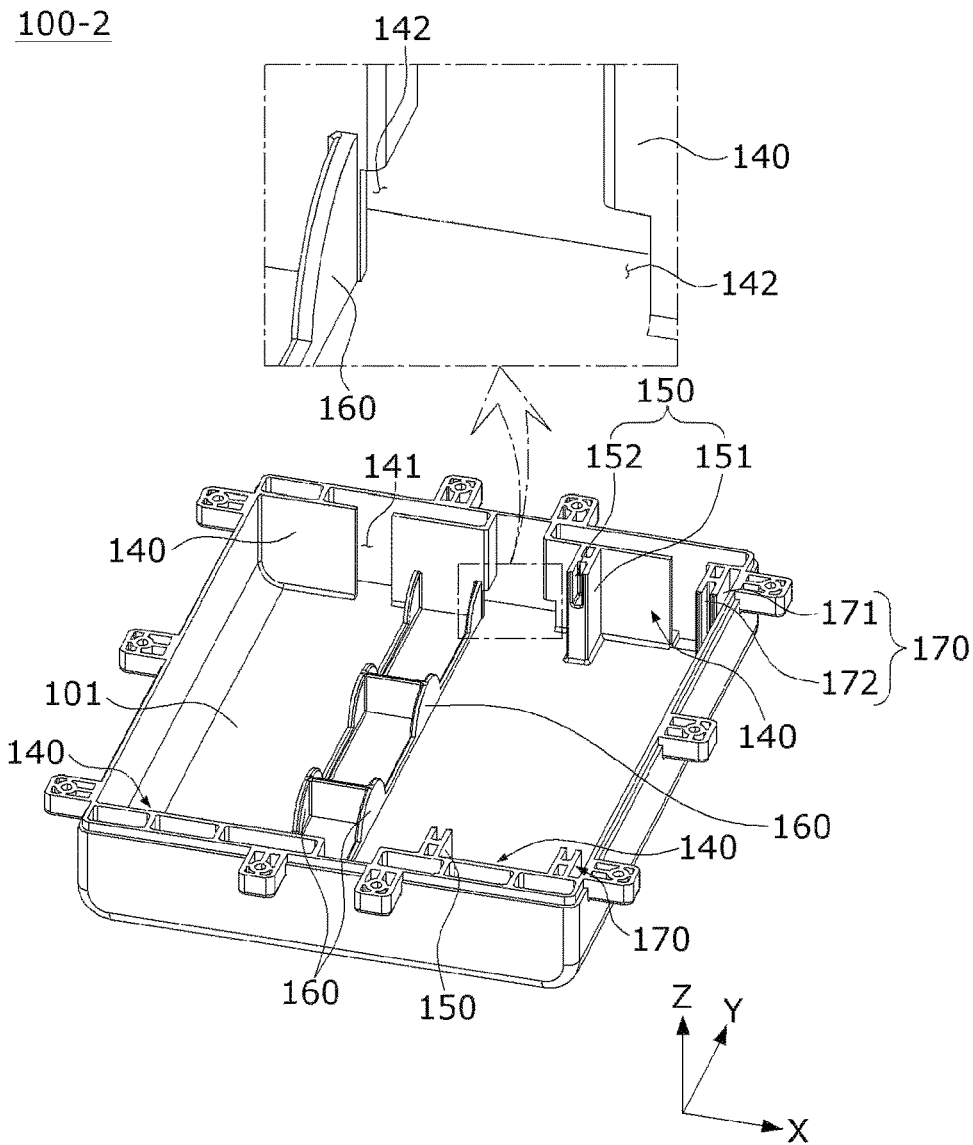
[FIG. 11]
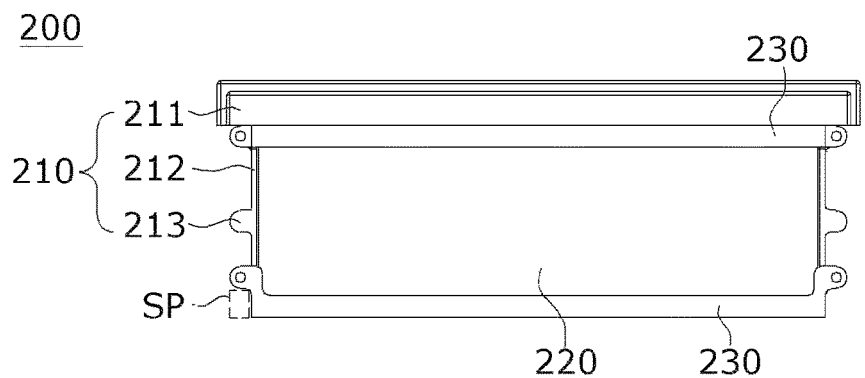

[FIG. 12]
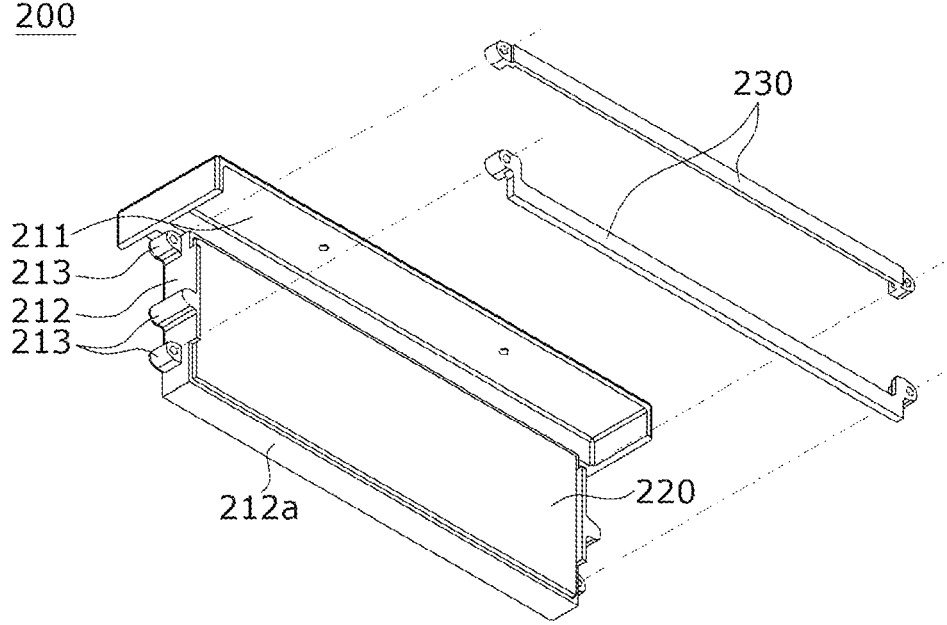
[FIG. 13]
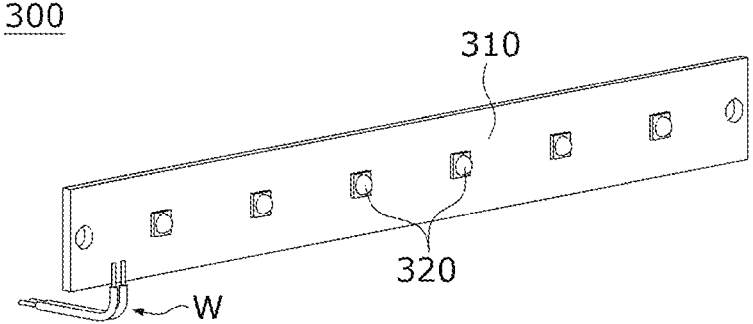
[FIG. 14]
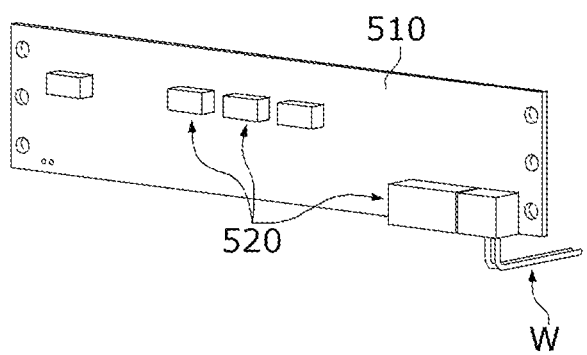

[FIG. 15]
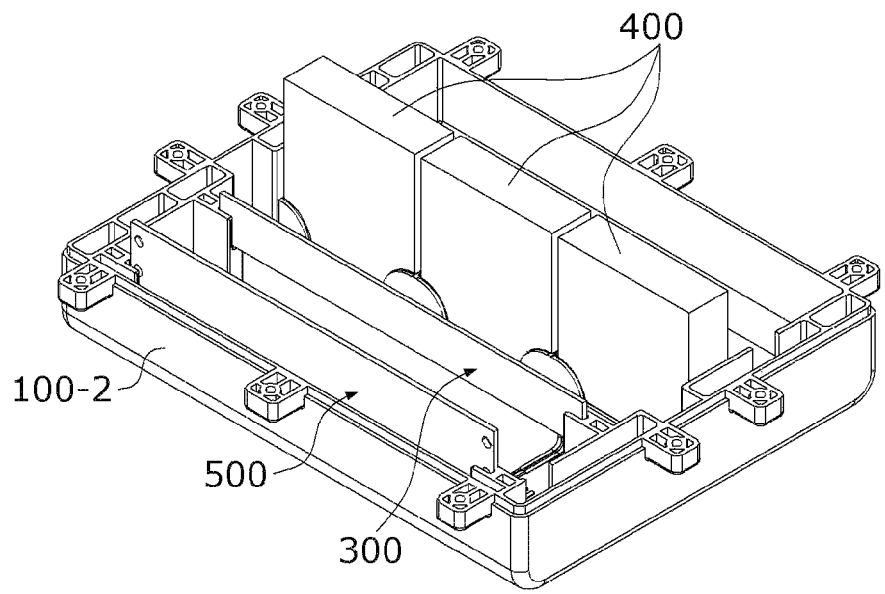
[FIG. 16]
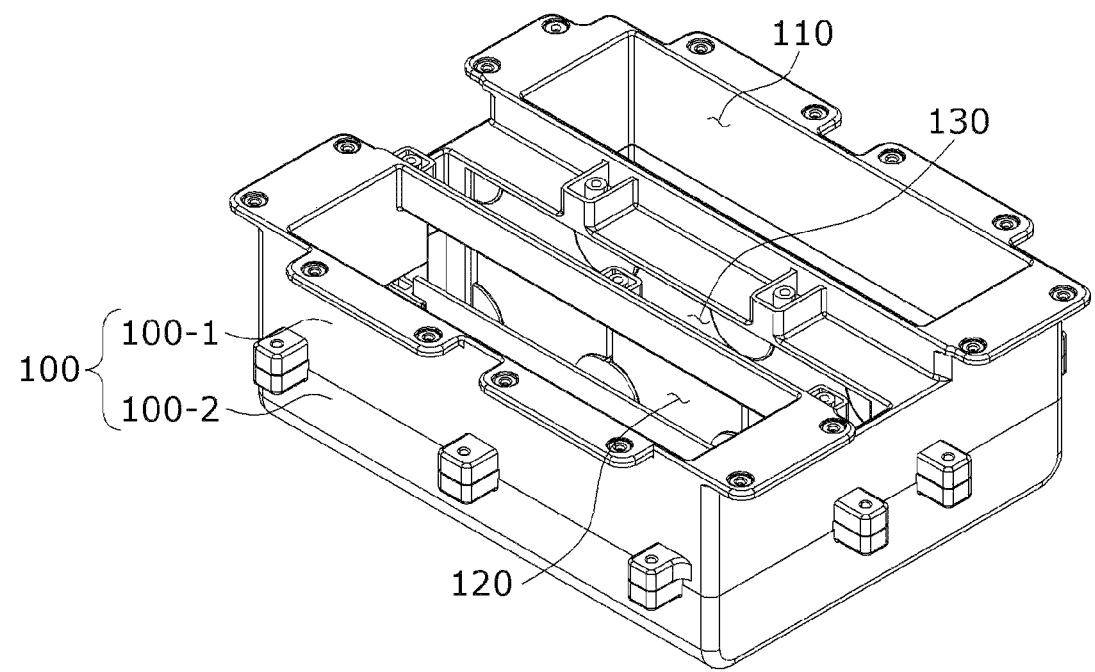

[FIG. 17]
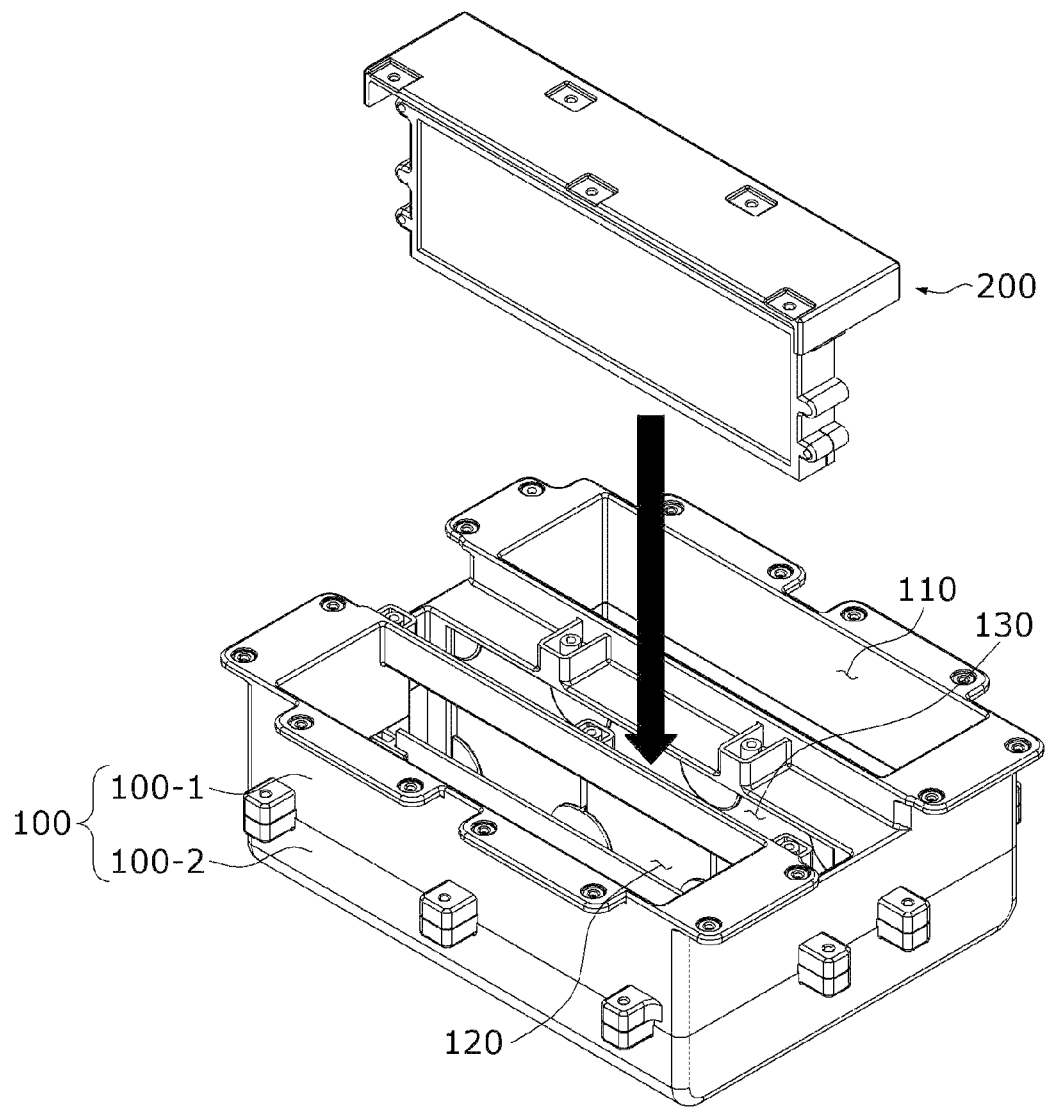

[FIG. 18]
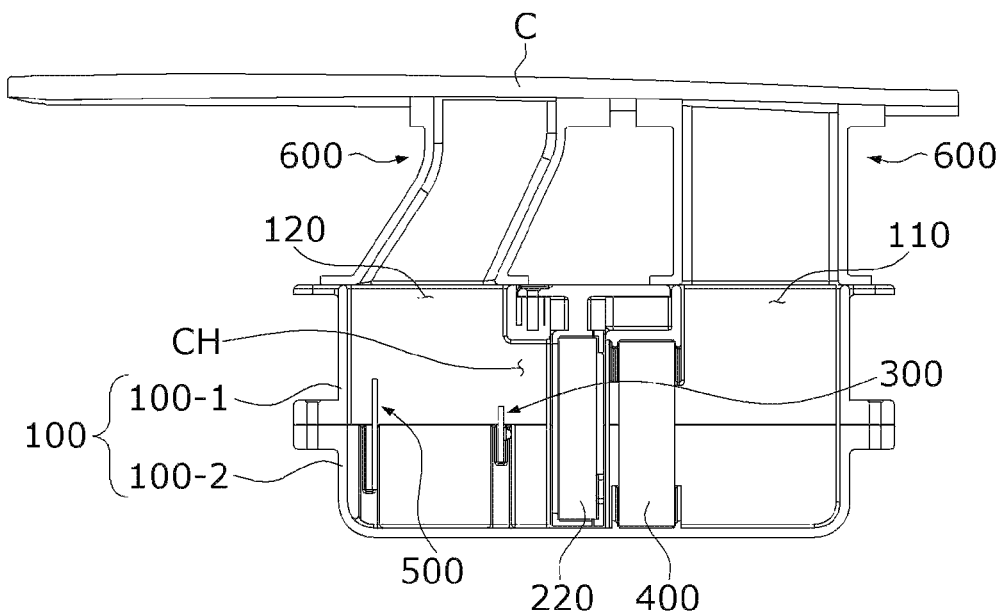
[FIG. 19]
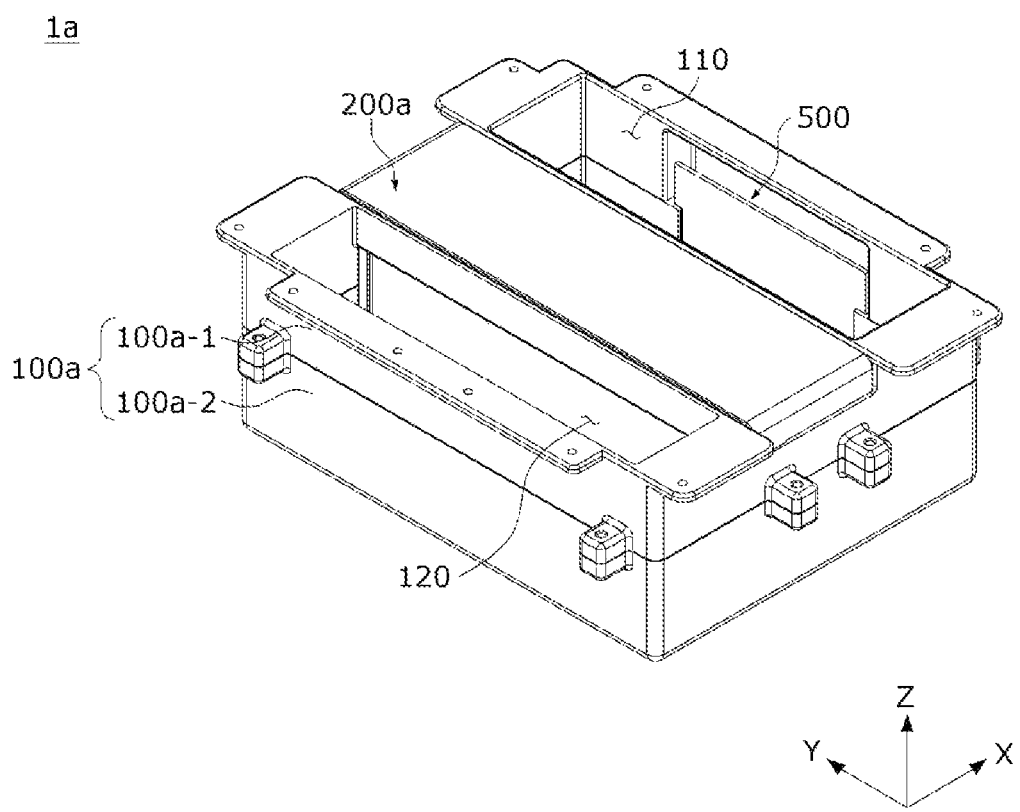

[FIG. 20]
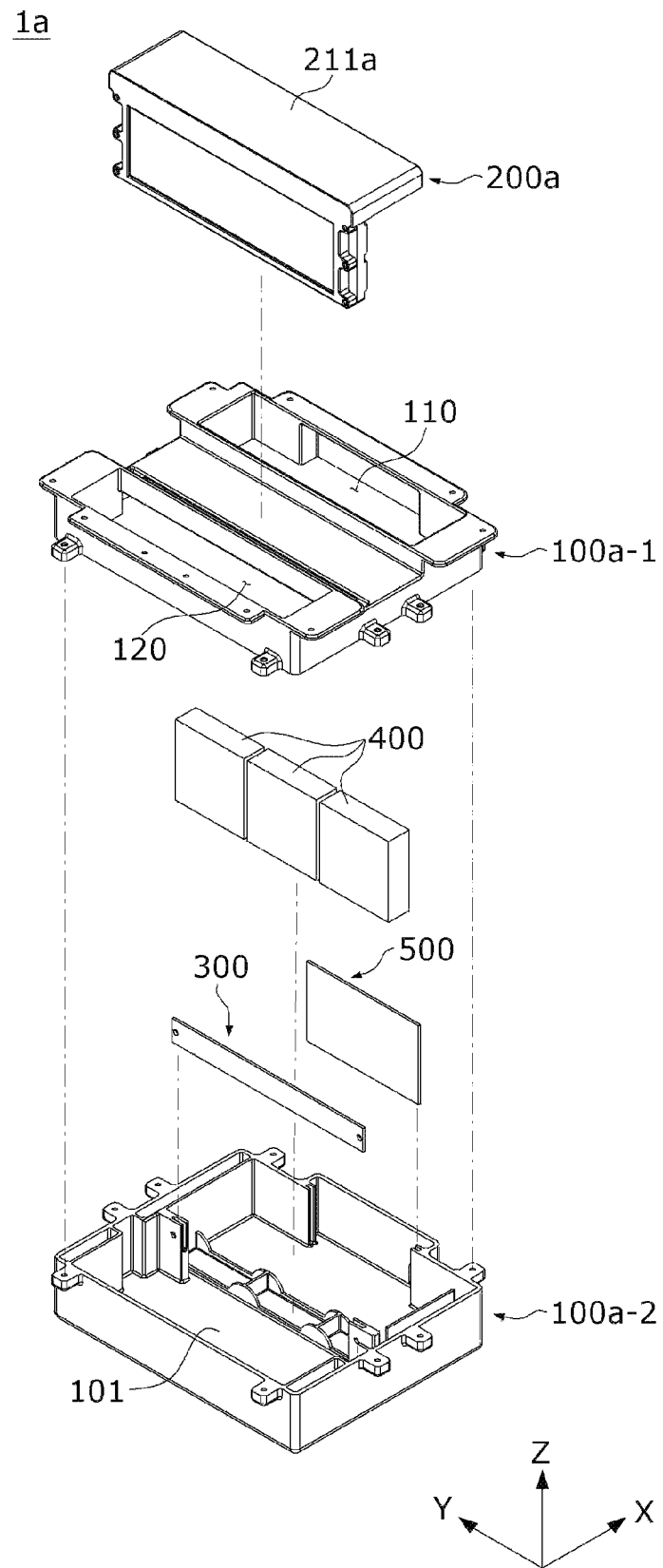

[FIG. 21]
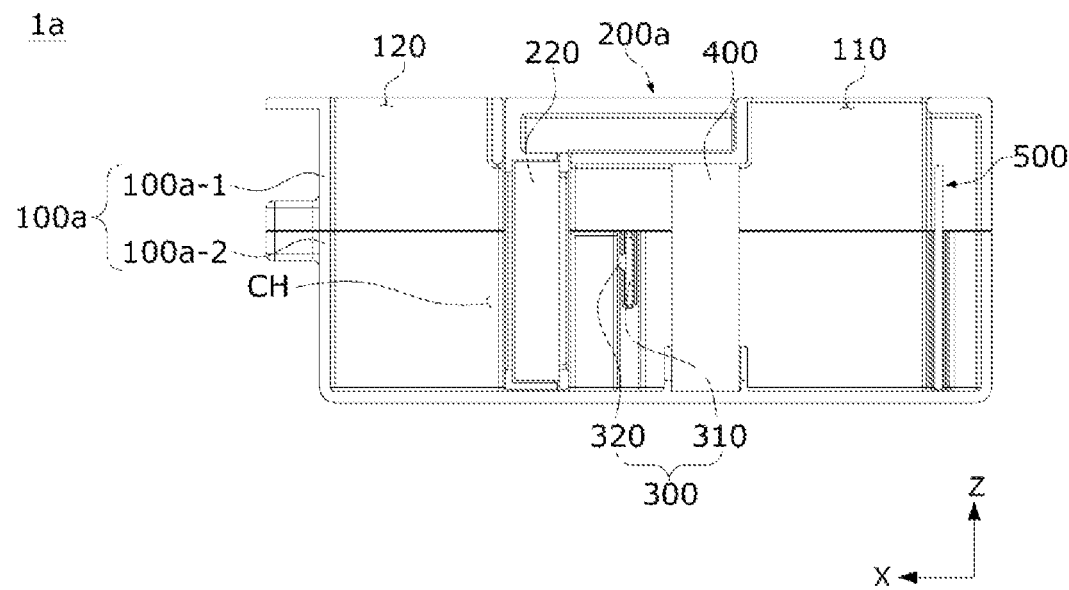
[FIG. 22]
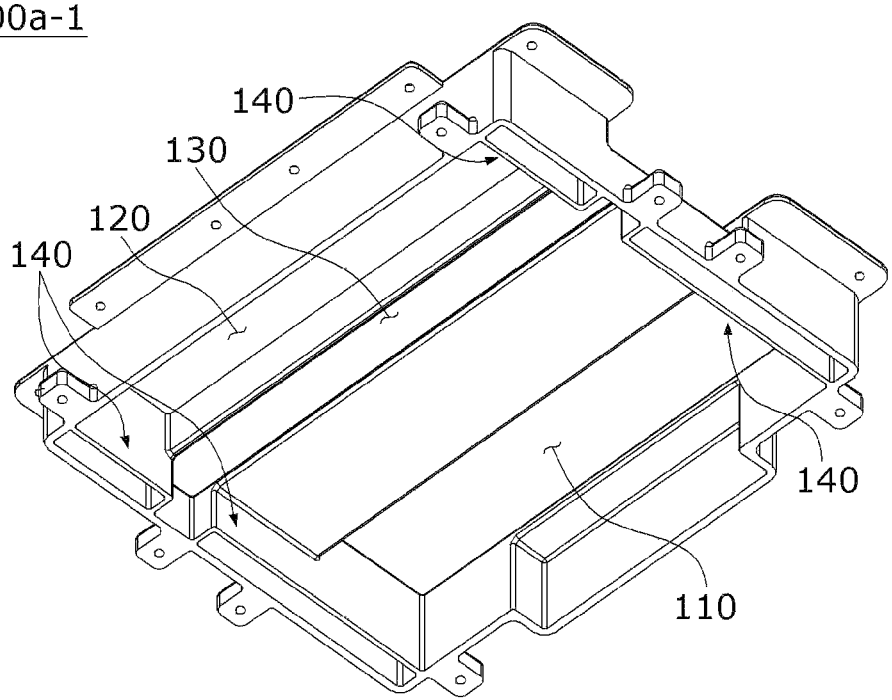

[FIG. 23]
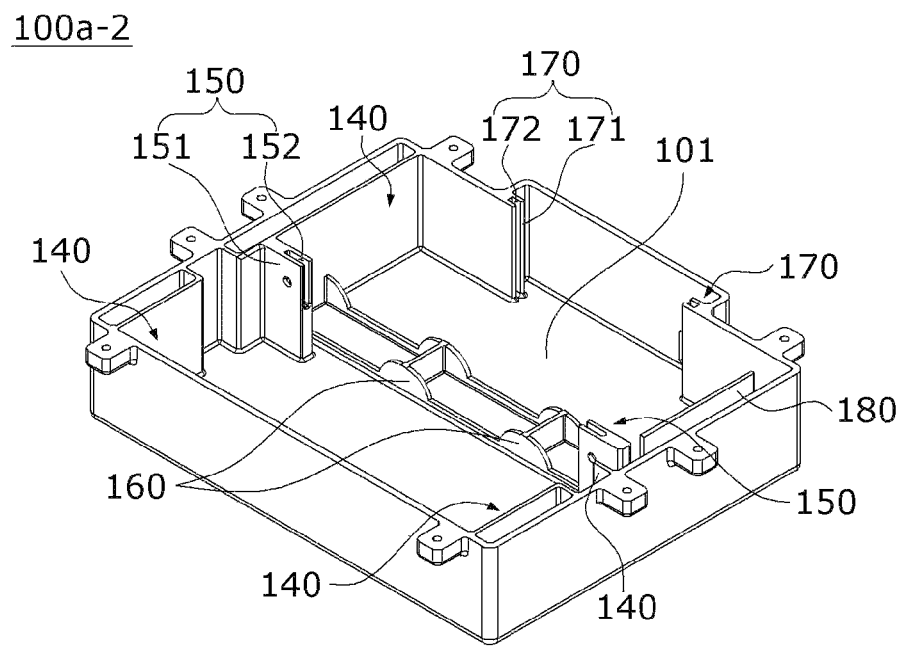

[FIG. 24]
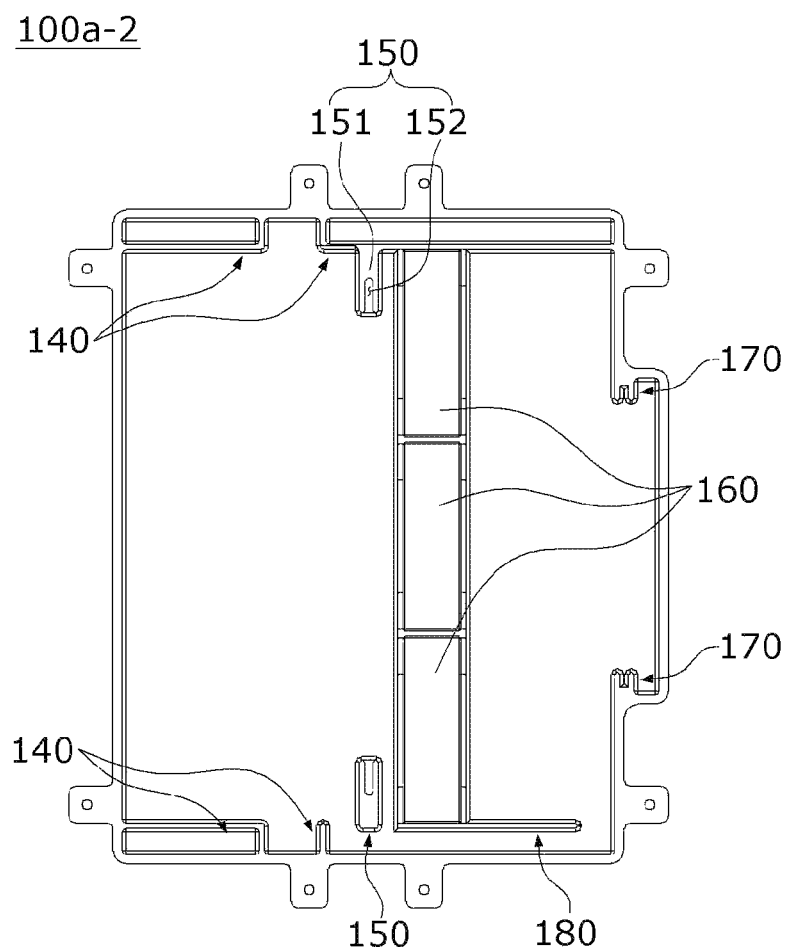

[FIG. 25]
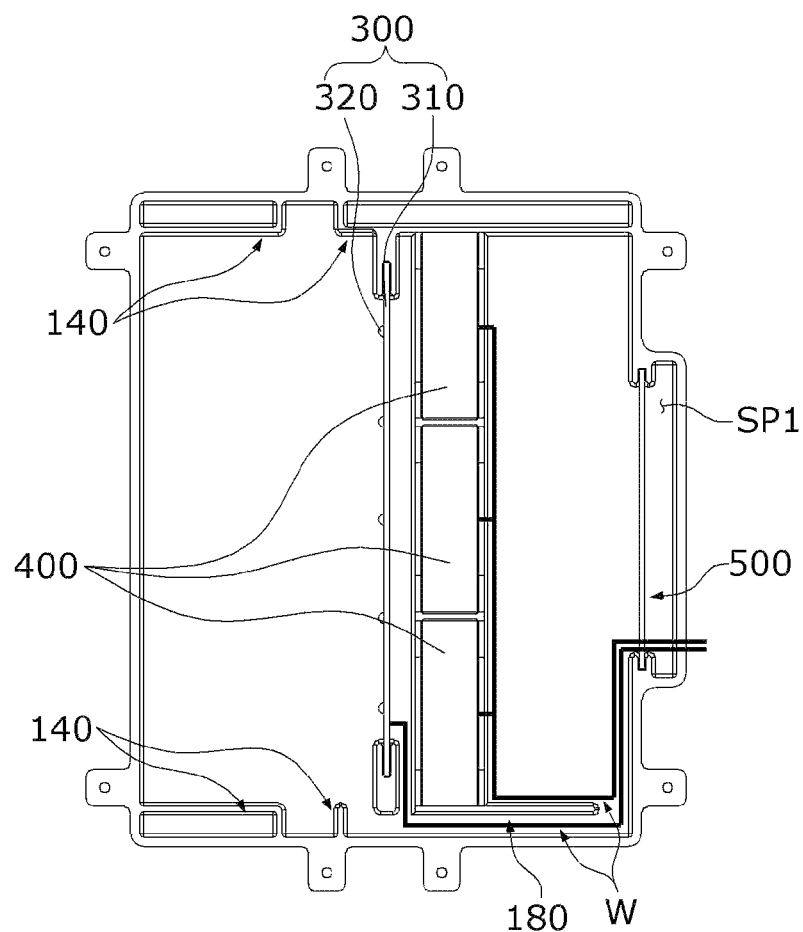
[FIG. 26]
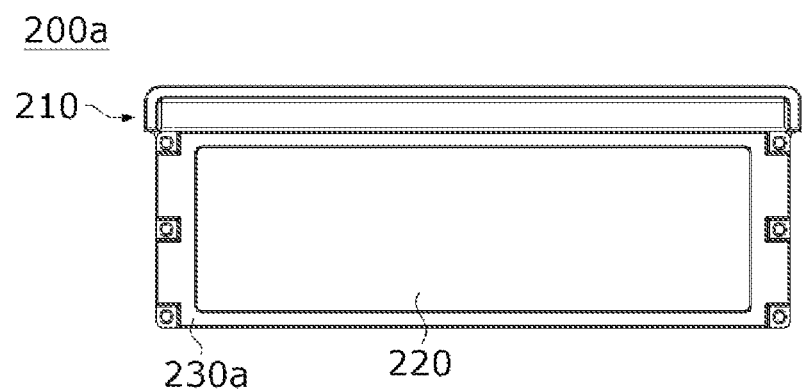

[FIG. 27]
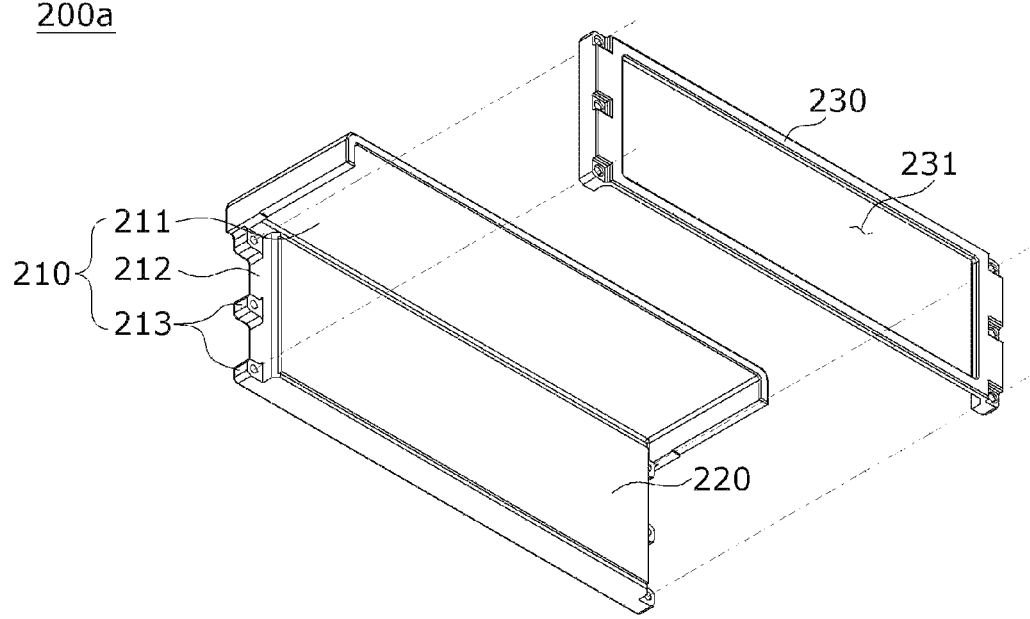
[FIG. 28]
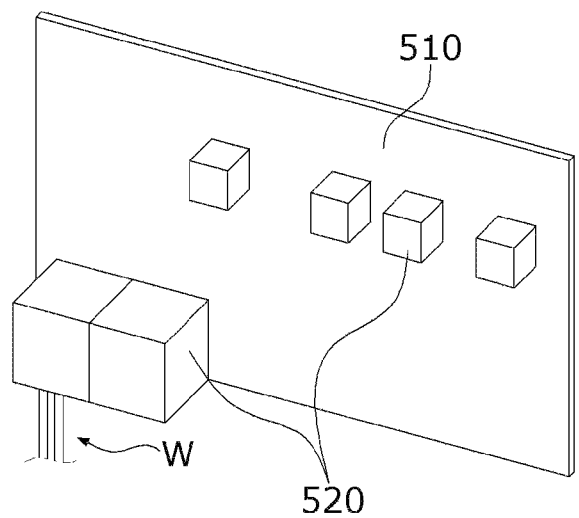

[FIG. 29]
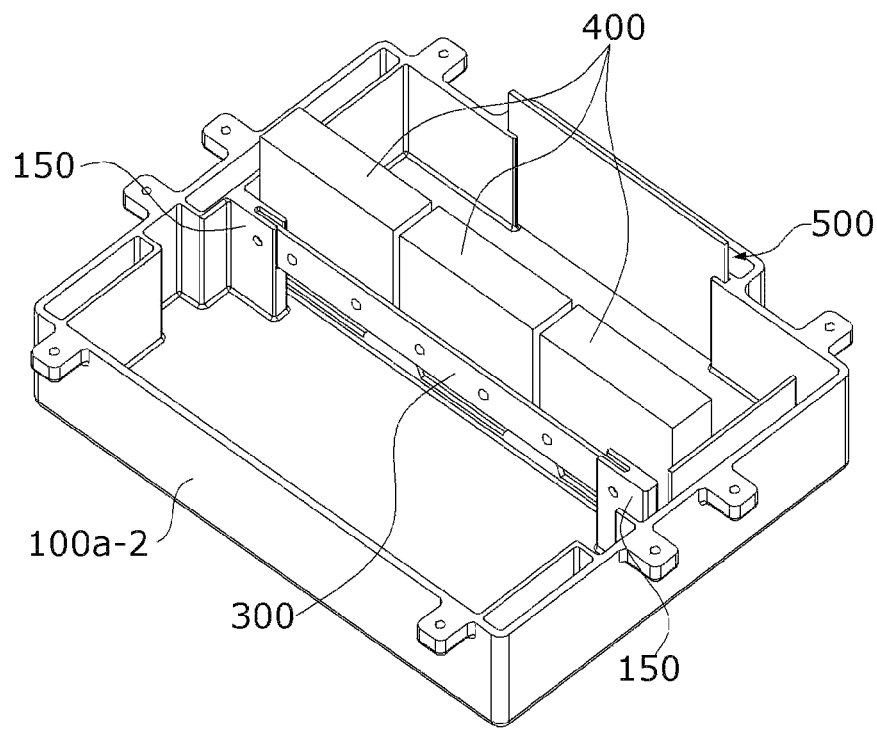
[FIG. 30]
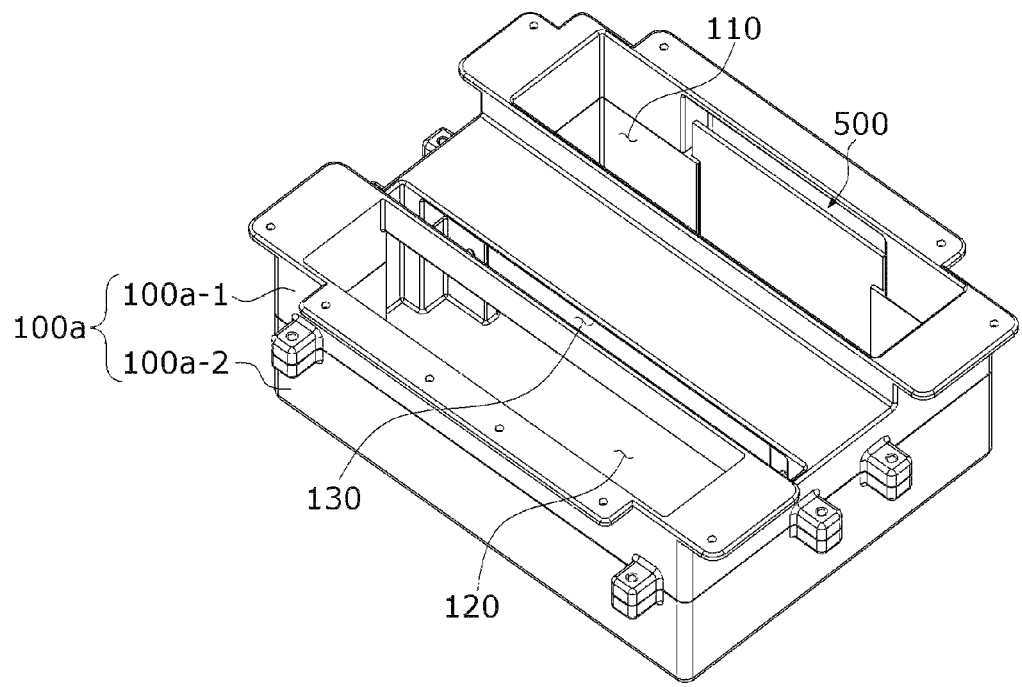

[FIG. 31]
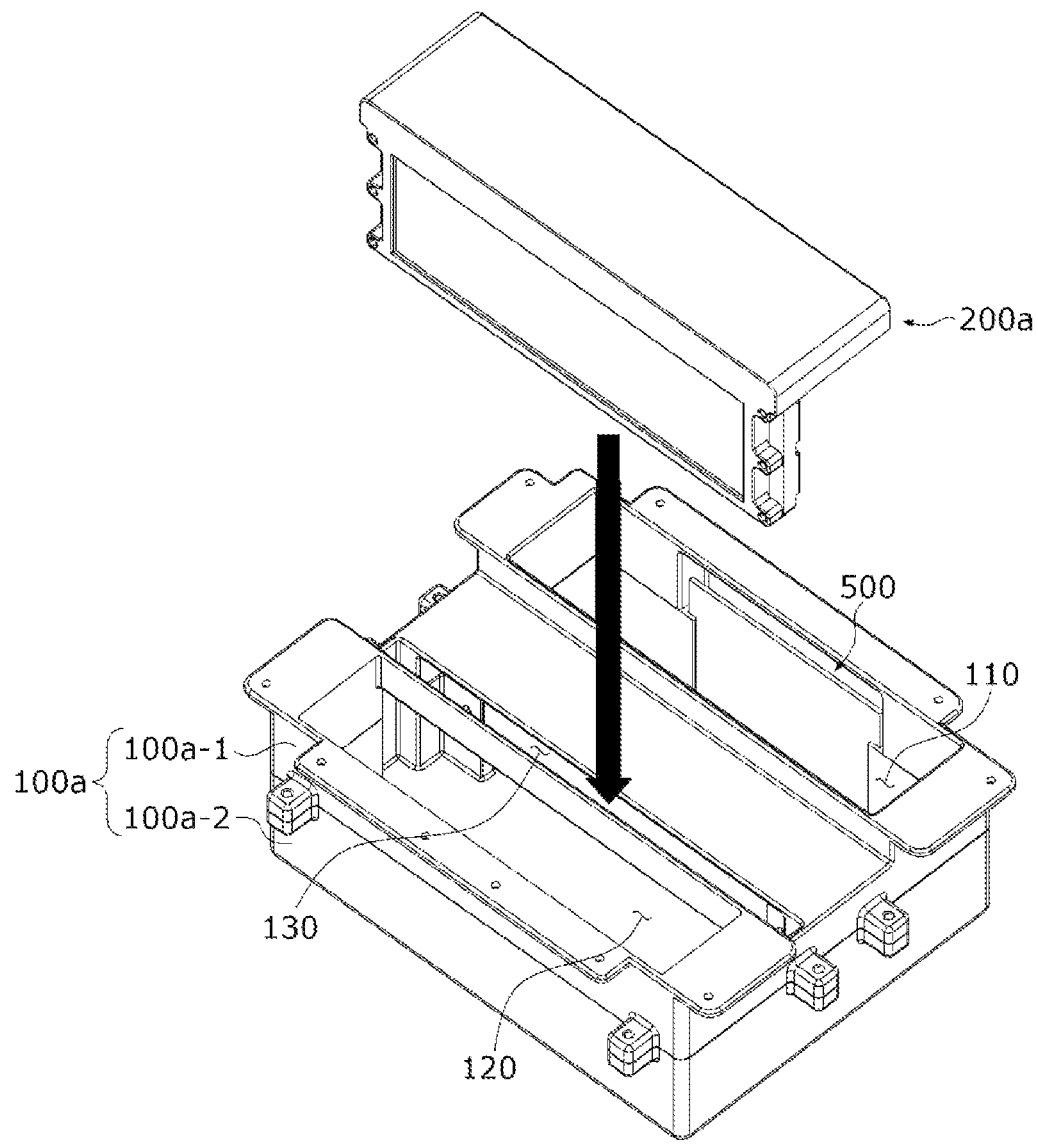

VEHICLE STERILIZING APPARATUS AND COCKPIT MODULE HAVING THE SAME

CROSS-REFERENCE TO RELATED APPLICATION

This application claims priority to and the benefit of Korean Patent Application No. 10-2021-0189912, filed on Dec. 28, 2021, the disclosure of which is incorporated herein by reference in its entirety.

BACKGROUND

1. Technical Field

The present disclosure relates to a vehicle sterilizing apparatus and a cockpit module including the same. Specifically, the present disclosure relates to a vehicle sterilizing apparatus, which is installed in a cockpit module in order to improve vehicle interior hygiene, and a cockpit module including the same.

2. Discussion of Related Art

A vehicle is used as a means for transportation which is frequently used by people. In addition, as interest in the COVID-19 pandemic and car sharing has been growing, interest in improvement of people's hygiene is growing.

Accordingly, there is a need to regularly sterilize an interior of a vehicle for public hygiene.

Currently, although an automated cleaning system for cleaning an exterior of a vehicle is widely used as an apparatus for maintaining the cleanness of the vehicle, since the automated cleaning system uses water or washing liquid in a liquid state, there is a limitation in the means for cleaning a vehicle interior.

Accordingly, a simple and efficient means for sterilizing the vehicle interior is required in order not only to clean a vehicle exterior for maintaining the cleanness thereof but also to maintain the cleanness of the interior.

However, most disinfection devices for disinfecting a vehicle interior are devices for simply disinfecting a vehicle using simple spray devices.

Accordingly, a vehicle sterilizing apparatus capable of improving the cleanness of a vehicle interior, the ease of assembly for after sales service (A/S), and a degree of design freedom is required.

SUMMARY

The present disclosure is directed to providing a vehicle sterilizing apparatus in which a sterilizing apparatus is implemented in a cockpit module in order to improve vehicle interior hygiene and a cockpit module including the same.

The present disclosure is also directed to providing a vehicle sterilizing apparatus, which is independently driven using a separate flow channel distinguished from a vehicle air conditioner, and a cockpit module including the same.

The present disclosure is also directed to providing a vehicle sterilizing apparatus with improved ease of filter module replacement and a cockpit module including the same.

Objectives to be solved by the present disclosure is not limited to the above-described objectives, and other objectives, which are not described above, will be clearly understood by those skilled in the art through a description below.

According to an aspect of the present disclosure, there is provided a sterilizing apparatus including a housing including an inlet port, an outlet port, a flow channel connecting the inlet port and the outlet port, and a hole communicating with the flow channel, a filter module disposed in the flow channel, a sterilization unit which emits ultraviolet rays toward the filter module, and a fan which moves air introduced through the inlet port to the outlet port, in which the filter module is inserted into and installed in the housing through the hole.

In this case, the filter module may include a filter bracket, a filter disposed on the filter bracket, and a support member which fixes the filter to the filter bracket, in which the filter may be disposed between the fan and the sterilization unit.

The filter bracket may include a plate portion, a wall portion extending downward from the plate portion, and a plurality of guide protrusions protruding from a side surface of the wall portion, in which the guide protrusion disposed at a lowermost end among the plurality of guide protrusions may be disposed to have a predetermined difference in height when compared to a lower surface of the wall portion.

The first support member may have a bar shape.

The housing may include a first guide protruding from a bottom surface thereof, and the first guide may guide an arrangement of the filter module.

The sterilization unit may include a first substrate and at least one light source which is mounted on the first substrate and emits the ultraviolet rays toward the filter of the filter module, in which the first substrate may be disposed at a predetermined height due to a second guide protruding from a bottom surface of the housing.

The first substrate may include a metal material.

The sterilizing apparatus may further include a control unit electrically connected to the sterilization unit and the fan, in which a second substrate of the control unit may be disposed in a lower portion of the outlet port.

The second substrate may be disposed to be spaced apart from the first substrate, and a size of the second substrate may be greater than a size of the first substrate.

The fan may be disposed as a plurality of fans in the housing, and the control unit may individually control the plurality of fans.

Meanwhile, the sterilizing apparatus may further include a duct member disposed on the outlet port.

The sterilizing apparatus may further include a cover disposed to cover the inlet port and the outlet port. the cover may have a hole disposed to face the inlet port and the outlet port, and one region of the cover may be disposed to overlap a speaker.

The filter module may include a filter bracket, a filter disposed on the filter bracket, and a second support member which fixes the filter to the filter bracket, in which the sterilization unit may be disposed between the filter and the fan.

In this case, the second support member may have a quadrangular frame shape and include a hole at a center thereof.

The sterilization unit may include a first substrate and at least one light source which is mounted on the first substrate and emits the ultraviolet rays toward the filter of the filter module, in which the first substrate may be disposed at a predetermined height due to a second guide protruding from a bottom surface of the housing.

The sterilizing apparatus may further include a control unit electrically connected to the sterilization unit and the fan, in which a second substrate of the control unit may be disposed in a lower portion of the inlet port.

The sterilizing apparatus may further include a control unit electrically connected to the sterilization unit and the fan, in which a guide coupled to the control unit may include a protruding portion and a groove, and one side wall surface of the protruding portion may be coplanar with one side wall surface constituting the inlet port.

The second substrate on which a plurality of elements are disposed may be disposed to be spaced apart from the first substrate, and a size of the second substrate may be greater than a size of the first substrate.

The fan disposed to face the second substrate may be disposed as a plurality of fans in the housing, and the control unit individually controls the plurality of fans.

The second substrate may be electrically connected to the sterilization unit and the fan by a wire, and the housing may include a guide wall so that the wire bypasses the fan and is connected to the sterilization unit.

Meanwhile, the filter may be a photocatalytic filter which reacts to the ultraviolet rays.

According to another aspect of the present disclosure, there is provided a cockpit module including a crash pad, a sterilizing apparatus detachably disposed on the crash pad, a speaker disposed on the crash pad, and a cover disposed to cover the speaker. The cover may have a hole disposed to face an inlet port and an outlet port of the sterilizing apparatus.

In this case, the sterilizing apparatus may include a housing including the inlet port, the outlet port, a flow channel connecting the inlet port and the outlet port, and a hole communicating with the flow channel, a filter module disposed in the flow channel, a sterilization unit which emits ultraviolet rays toward the filter module, and a fan which moves air introduced through the inlet port to the outlet port, in which the filter module may be inserted into and installed in the housing through the hole.

The filter module may include a filter bracket, a filter disposed on the filter bracket, and a first support member which fixes the filter to the filter bracket, and the filter may be disposed between the fan and the sterilization unit.

The cockpit module may further include a control unit electrically connected to the sterilization unit and the fan, in which a second substrate of the control unit may be disposed in a lower portion of the outlet port.

The cockpit module may further include a duct member disposed between the outlet port and the cover.

The filter module may include a filter bracket, a filter disposed on the filter bracket, and a second support member which fixes the filter to the filter bracket, in which the sterilization unit may be disposed between the filter and the fan.

In this case, the cockpit module may further include a control unit electrically connected to the sterilization unit and the fan, in which a second substrate of the control unit may be disposed in a lower portion of the inlet port.

According to still another aspect of the present disclosure, there is provided a cockpit module including a crash pad, a speaker and a sterilizing apparatus which are disposed on the crash pad, and a cover detachably disposed on the crash pad to cover the speaker and the sterilizing apparatus, in which, when the cover is removed, a filter module disposed in the sterilizing apparatus is exposed.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 1 is a view illustrating a cockpit module in which a vehicle sterilizing apparatus according to an embodiment is disposed;

FIG. 2A is a view illustrating a vehicle sterilizing apparatus according to an embodiment in which a cover is disposed;

FIG. 2B is a view illustrating the vehicle sterilizing apparatus according to the embodiment from which the cover is removed;

FIG. 3 is a view illustrating replacement of a filter module disposed in a vehicle sterilizing apparatus according to an embodiment;

FIG. 4 is a perspective view illustrating a vehicle sterilizing apparatus according to a first embodiment;

FIG. 5 is an exploded perspective view illustrating the vehicle sterilizing apparatus according to the first embodiment;

FIG. 6 is a cross-sectional view illustrating the vehicle sterilizing apparatus according to the first embodiment;

FIG. 7 is a perspective view illustrating a housing of the vehicle sterilizing apparatus according to the first embodiment;

FIG. 8 is a plan view illustrating the housing of the vehicle sterilizing apparatus according to the first embodiment;

FIG. 9 is a bottom perspective view illustrating an upper housing of the vehicle sterilizing apparatus according to the first embodiment;

FIG. 10 is a perspective view illustrating a lower housing of the vehicle sterilizing apparatus according to the first embodiment;

FIG. 11 is a front view illustrating a filter module disposed in the vehicle sterilizing apparatus according to the first embodiment;

FIG. 12 is an exploded perspective view illustrating the filter module disposed in the vehicle sterilizing apparatus according to the first embodiment;

FIG. 13 is a perspective view illustrating a sterilization unit disposed in the vehicle sterilizing apparatus according to the first embodiment;

FIG. 14 is a perspective view illustrating a control unit disposed in the vehicle sterilizing apparatus according to the first embodiment;

FIG. 15 is a view illustrating an arrangement relationship between the lower housing, the sterilization unit, a fan, and the control unit which are disposed in the vehicle sterilizing apparatus according to the first embodiment;

FIG. 16 is a view illustrating an arrangement relationship between the upper housing and the lower housing which are disposed in the vehicle sterilizing apparatus according to the first embodiment;

FIG. 17 is a view illustrating an arrangement relationship between the housing and the filter module which are disposed in the vehicle sterilizing apparatus according to the first embodiment;

FIG. 18 is a view illustrating a duct member disposed in the vehicle sterilizing apparatus according to the first embodiment;

FIG. 19 is a perspective view illustrating a vehicle sterilizing apparatus according to a second embodiment;

FIG. 20 is an exploded perspective view illustrating the vehicle sterilizing apparatus according to the second embodiment;

FIG. 21 is a cross-sectional view illustrating the vehicle sterilizing apparatus according to the second embodiment;

FIG. 22 is a bottom perspective view illustrating an upper housing of the vehicle sterilizing apparatus according to the second embodiment;

FIG. 23 is a perspective view illustrating a lower housing of the vehicle sterilizing apparatus according to the second embodiment;

FIG. 24 is a plan view illustrating the lower housing of the vehicle sterilizing apparatus according to the second embodiment;

FIG. 25 is a plan view illustrating the lower housing, a sterilization unit, and a fan of the vehicle sterilizing apparatus according to the second embodiment;

FIG. 26 is a front view illustrating a filter module disposed in the vehicle sterilizing apparatus according to the second embodiment;

FIG. 27 is an exploded perspective view illustrating the filter module disposed in the vehicle sterilizing apparatus according to the second embodiment;

FIG. 28 is a perspective view illustrating a control unit disposed in the vehicle sterilizing apparatus according to the second embodiment;

FIG. 29 is a view illustrating an arrangement relationship between the lower housing, the sterilization unit, a fan, and the control unit which are disposed in the vehicle sterilizing apparatus according to the second embodiment;

FIG. 30 is a view illustrating an arrangement relationship between the upper housing and the lower housing which are disposed in the vehicle sterilizing apparatus according to the second embodiment; and FIG. 31 is a view illustrating an arrangement relationship between a housing and the filter module which are disposed in the vehicle sterilizing apparatus according to the second embodiment.

DETAILED DESCRIPTION OF EXEMPLARY EMBODIMENTS

Since the present disclosure allows various changes and has many embodiments, specific embodiments will be illustrated in the accompanying drawings and described. However, this is not intended to limit the present disclosure to the specific embodiments, and it is to be appreciated that all changes, equivalents, and substitutes that fall within the spirit and technical scope of the present disclosure are encompassed in the present disclosure.

Although the terms "first," "second," and the like may be used herein to describe various elements, these elements should not be limited by these terms. These terms are only used to distinguish one element from another element. For example, a second element could be termed a first element, and a first element could similarly be termed a second element without departing from the scope of the present disclosure. The term "and/or" includes any one or any combination among a plurality of associated listed items.

When an element is referred to as being "connected" or "coupled" to another element, it will be understood that the element can be directly connected or coupled to another element, or other elements may be present therebetween. In contrast, when an element is referred to as being "directly connected" or "directly coupled" to another element, it will be understood that there are no intervening elements.

In a description of the embodiment, in a case in which any one element is described as being formed on or under another element, such a description includes both a case in which the two elements are formed to be in direct contact with each other and a case in which the two elements are in indirect contact with each other such that one or more other elements are interposed between the two elements. In addition, when one element is described as being formed on or under another element, such a description may include a case in which the one element is formed at an upper side or a lower side with respect to another element.

The terminology used herein is for the purpose of describing particular embodiments only and is not intended to limit the present disclosure. The singular forms are intended to include the plural forms unless the context clearly indicates otherwise. In the present specification, it should be further understood that the terms "comprise," "comprising," "include," and/or "including," when used herein, specify the presence of stated features, numbers, steps, operations, elements, and/or components but do not preclude the presence or addition of one or more other features, numbers, steps, operations, elements, components, and/or groups thereof.

Unless otherwise defined, all terms including technical and scientific terms used herein have meanings which are the same as meanings generally understood by those skilled in the art. Terms, such as those defined in commonly used dictionaries, should be interpreted as having meanings that are consistent with their meanings in the contexts of the relevant art and will not be interpreted in an idealized or overly formal sense unless expressly so defined here.

Hereinafter, when embodiments are described in detail with reference to the accompanying drawings, components that are the same or correspond to each other will be denoted by the same reference numerals regardless of the reference numerals, and redundant descriptions will be omitted.

As interest in improvement of occupant hygiene increases, a vehicle may include a separate sterilizing apparatus in addition to an air conditioner providing a conditioned environment to a vehicle interior. In this case, the air conditioner may adjust a temperature, a humidity, cleanliness, and air ventilation using a heat exchanger and the like, such as an evaporator and a heater.

However, since the sterilizing apparatus is formed to have a predetermined size, there is a problem in that a degree of design freedom of the vehicle interior is reduced.

Accordingly, since the vehicle sterilizing apparatus according to an embodiment is disposed in a cockpit module, vehicle interior hygiene and a degree of design freedom may be improved.

Specifically, since the sterilizing apparatus may be detachably disposed on a lower portion of the crash pad, a degree of design freedom of the vehicle interior is secured, and occupant hygiene and convenience of maintenance may be improved. In this case, the cockpit module may be provided as a module which is disposed in front of a driver seat and a passenger seat so that an engine room is partitioned from the vehicle interior. In addition, a steering wheel, an instrument panel, a glove box, an airbag apparatus, a display device, an audio device, a duct of an air conditioner, and the like may be installed in the cockpit module.

FIG. 1 is a view illustrating a cockpit module in which a vehicle sterilizing apparatus according to an embodiment is disposed. In addition, FIG. 2 shows views illustrating an arrangement relationship between the vehicle sterilizing apparatus according to the embodiment, a speaker, and a cover, wherein FIG. 2A is the view illustrating the vehicle sterilizing apparatus according to the embodiment in which the cover is disposed, and FIG. 2B is the view illustrating the vehicle sterilizing apparatus according to the embodiment from which the cover is removed. In addition, FIG. 3 is a view illustrating replacement of a filter module disposed in a vehicle sterilizing apparatus according to an embodiment.

In this case, an X direction illustrated in FIG. 1 may be a front-rear direction, and a Z direction may be a vertical direction. In addition, a Y direction illustrated in FIG. 2 may be a vehicle width direction or left-right direction. In addition, the vertical direction may include an upward direction toward a ceiling of a vehicle and a downward direction opposite to the upward direction. In addition, the front-rear direction may include a forward direction and a rearward direction opposite to the forward direction based on a main driving direction of the vehicle. In addition, an arrow illustrated in FIG. 1 may denote a flow of air.

In addition, a reference character "D" illustrated in FIG. 1 may denote a duct connected to a vehicle air conditioner, and a reference character "M" may denote a display device such as a monitor disposed so that an occupant may check information of the vehicle. In addition, a reference character "WS" illustrated in FIG. 1 may denote a windshield of the vehicle. In this case, the windshield may be referred to as a front glass. In addition, a reference character "G" illustrated in FIG. 2 may denote a glove box.

Referring to FIGS. 1 and 2, the cockpit module according to the embodiment may include a speaker S disposed in a crash pad P, a cover C disposed to cover the speaker S, and a vehicle sterilizing apparatus 1 or 1a according to the embodiment disposed on a lower portion of the crash pad P. In this case, the crash pad P may be referred to as a dashboard.

Since the sterilizing apparatus 1 or 1a is disposed to be hidden by the crash pad P and the cover C, the sterilizing apparatus 1 or 1a may not occupy a separate space in a vehicle interior. Accordingly, the sterilizing apparatus 1 or 1a may improve a degree of design freedom of the vehicle interior.

The cover C may be disposed on the speaker S and may include a plurality of holes H. Accordingly, a sound generated by the speaker S may be transmitted to the vehicle interior through the holes H. In this case, an inlet port 110 and an outlet port 120 of the sterilizing apparatus 1 or 1a may share the holes H of the cover C along with the speaker S. As illustrated in FIG. 2A, some of the holes H may be disposed to overlap the inlet port 110 and the outlet port 120 in the vertical direction.

In addition, the sterilizing apparatus 1 or 1a may be disposed in front of the monitor M and may sterilize air flowing above the crash pad P.

In addition, the sterilizing apparatus 1 or 1a may be disposed to be spaced apart from the duct D. Accordingly, the sterilizing apparatus 1 or 1a may be used as a separate air conditioner in addition to the air conditioner. That is, the sterilizing apparatus 1 or 1a may be independently driven. For example, since the sterilizing apparatus 1 or 1a may include the filter module and may be separately disposed from the duct D, the sterilizing apparatus 1 or 1a may be used as an independently driven auxiliary air conditioner.

Furthermore, since the sterilizing apparatus 1 or 1a may further include a heat exchanger (not shown) disposed therein, the sterilizing apparatus 1 or 1a may also adjust a temperature of air in the vehicle interior. In this case, a positive temperature coefficient (PTC) heater or the like may be used as the heat exchanger.

Meanwhile, the sterilizing apparatus 1 or 1a may include the inlet port 110 and the outlet port 120, and the inlet port 110 may be disposed behind the outlet port 120. That is, the inlet port 110 may be disposed to be closer to the vehicle interior or occupant than the outlet port 120 to improve a sterilization effect.

In addition, as illustrated in FIG. 1, the outlet port 120 may be disposed to be closer to the windshield WS than the inlet port 110. Accordingly, air discharged through the outlet port 120 is guided by the windshield WS to be spread in the vehicle interior. In this case, since the air may be mixed with air discharged through the duct D and may circulate in the vehicle interior, circularity of the air discharged through the outlet port 120 may be improved.

In addition, when the cover C is removed, a filter module 200 of the sterilizing apparatus 1 or 1a may be exposed. Accordingly, as illustrated in FIG. 3, the filter module 200 may be easily replaced in the sterilizing apparatus 1 or 1a.

First Embodiment

FIG. 4 is a perspective view illustrating a vehicle sterilizing apparatus according to a first embodiment, FIG. 5 is an exploded perspective view illustrating the vehicle sterilizing apparatus according to the first embodiment, FIG. 6 is a cross-sectional view illustrating the vehicle sterilizing apparatus according to the first embodiment, FIG. 7 is a perspective view illustrating a housing of the vehicle sterilizing apparatus according to the first embodiment, FIG. 8 is a plan view illustrating the housing of the vehicle sterilizing apparatus according to the first embodiment, FIG. 9 is a bottom perspective view illustrating an upper housing of the vehicle sterilizing apparatus according to the first embodiment, and FIG. 10 is a perspective view illustrating a lower housing of the vehicle sterilizing apparatus according to the first embodiment.

Referring to FIGS. 4 to 6, a sterilizing apparatus 1 according to the embodiment may include a housing 100 including a flow channel CH formed therein to connect an inlet port 110 and an outlet port 120 and a hole 130 formed to communicate with the flow channel CH, a filter module 200 which filters air in the flow channel CH, a sterilization unit 300 which sterilizes a filter 220 of the filter module 200, fans 400 which move air introduced through the inlet port 110 to the outlet port 120, and a control unit 500. In this case, the control unit 500 may be electrically connected to the sterilization unit 300 and the fan 400 using wires W. In addition, the hole 130 may be referred to as a first hole, an insertion hole, or a first guide hole.

In this case, the filter module 200 may be detachably disposed in the housing 100 through the hole 130. Accordingly, the filter module 200 may be easily replaced. For example, a cover C is removed from a crash pad P, since the filter module 200 disposed in the hole 130 is exposed, the filter module 200 may be easily replaced.

The housing 100 may form an exterior of the sterilizing apparatus 1. In addition, the housing 100 may be detachably disposed on the crash pad P.

In addition, the housing 100 may include the inlet port 110, the outlet port 120, and the flow channel CH which connects the inlet port 110 and the outlet port 120. In addition, the housing 100 may include the hole 130 disposed between the inlet port 110 and the outlet port 120.

As illustrated in FIG. 6, the housing 100 may be formed in a "U" shape such that the inlet port 110 and the outlet port 120 are disposed to face the cover C.

The hole 130 may be formed to communicate with the flow channel CH to replace the filter module 200 and disposed between the inlet port 110 and the outlet port 120 so that the housing 100 may be implemented with a compact size.

The hole 130 may be disposed at a lower level than the inlet port 110 and the outlet port 120 based on an inner bottom surface of the housing 100. Accordingly, an upper surface 211a of a filter bracket 210 of the filter module 200 may be disposed to be coplanar with the inlet port 110 and the outlet port 120. In this case, the plane may be a virtual surface and may be a lower surface of the cover C. Accordingly, the upper surface 211a may support the cover C.

In addition, the housing 100 may include a plurality of guides which guide an arrangement of the filter module 200, the sterilization unit 300, the fan 400, the control unit 500, and the wires W. In this case, the guides may be provided as various shapes such as groove, wall, protrusion, and hole shapes.

The housing 100 may include a first guide 140 which guides an arrangement of the filter module 200.

The first guide 140 may be formed as a plurality of first guides 140 to protrude from a bottom surface 101 of the housing 100. In addition, the first guide 140 may support the filter module 200.

The housing 100 may include a second guide 150 which guides an arrangement of the sterilization unit 300.

The second guide 150 may include a first protruding portion 151 formed to protrude from the bottom surface 101 of the housing 100 and a first groove 152. In this case, the second guide 150 may be formed as two second guides 150 to face each other and to be spaced apart from each other in a Y direction. In addition, the second guide 150 may be formed to protrude from one side surface of the first guide 140 constituting the flow channel CH.

In addition, referring to FIGS. 6 and 8, the second guide 150 may be disposed to overlap a wall surface 121 at one side, which constitutes the outlet port 120, in a vertical direction. Accordingly, light leakage of light emitted from the sterilization unit 300 through the outlet port 120 may be minimized. In this case, the wall surface 121 may be referred to as a first outlet port surface, and the first outlet port surface may be a surface disposed adjacent to the filter module 200.

The first protruding portion 151 is formed to protrude from the bottom surface 101 of the housing 100 to allow the sterilization unit 300 to be positioned at a predetermined height.

The first groove 152 may be formed in an end portion of an upper side of the first protruding portion 151. In addition, one side of the sterilization unit 300 may be coupled to the first groove 152.

The housing 100 may include a third guide 160 which guides an arrangement of the fan 400.

The third guide 160 may be formed to protrude from the bottom surface 101 of the housing 100. In this case, the third guide 160 may be formed as a plurality of third guides 160 to correspond to the number of the fans 400 to support the fans 400.

The housing 100 may include a fourth guide 170 which guides an arrangement of the control unit 500.

The fourth guide 170 may include a second protruding portion 171, which is formed to protrude from the bottom surface 101 of the housing 100, and a second groove 172. In this case, the fourth guide 170 may be formed as two fourth guides 170 to face each other and to be spaced apart from each other in the Y direction.

In addition, the fourth guide 170 may be disposed to be adjacent to a wall surface 122 at the other side which constitutes the outlet port 120. Accordingly, the fourth guide 170 and the control unit 500 coupled to the fourth guide 170 may minimize interference with air discharged through the outlet port 120. In this case, the wall surface 122 may be referred to as a second outlet port surface, and the second outlet port surface may be a surface disposed to face the first outlet port surface.

The second protruding portion 171 may be formed to protrude from the bottom surface 101 of the housing 100 to allow the control unit 500 to be positioned at a predetermined height.

The second groove 172 may be concavely formed downward from an end portion of an upper side of the second protruding portion 171. In addition, one side of the control unit 500 may be coupled to the second groove 172.

The housing 100 may guide an arrangement of the wire W connected to the control unit 500 using a fifth guide. In this case, the fifth guide may be provided as a cut portion 141 formed in the first guide 140 and a hole 142. In this case, the hole 142 may be referred to as a second hole or second guide hole.

Accordingly, the wire W may bypass the sterilization unit 300, the fan 400, and the like through the fifth guide and may be connected to the fan 400. For example, the wire W electrically connecting the control unit 500 and the fan 400 may bypass the sterilization unit 300 and an end portion of the fan 400 in a width direction and may be connected to the fan 400.

Meanwhile, the housing 100 may be formed of at least two members for the sake of convenience in maintenance of components disposed therein.

Referring to FIGS. 6 and 7, the housing 100 may include an upper housing 100-1 and a lower housing 100-2. In this case, in order to distinguish the upper housing 100-1 and the lower housing 100-2 from those of a sterilizing apparatus according to a second embodiment, the upper housing 100-1 may be referred to as a first upper housing, and the lower housing 100-2 may be referred to as a first lower housing.

In the upper housing 100-1, the inlet port 110, the outlet port 120, the hole 130, the first guide 140, and the third guide 160 may be formed.

In the lower housing 100-2, the first guide 140 to the fifth guide may be formed.

Meanwhile, the upper housing 100-1 and the lower housing 100-2 may be coupled using a fastening member such as a bolt.

The filter module 200 may be provided as one module that is detachable from the housing 100 to be easily replaced. For example, the filter module 200 may be detachably disposed in the housing 100 through the hole 130 formed in the upper housing 100-1.

The filter 220 of the filter module 200 may filter foreign substances from air introduced into the housing 100. In addition, the filter 220 of the filter module 200 may sterilize the air. In this case, the filter 220 of the filter module 200 may be a photocatalytic filter. For example, as ultraviolet (UV) rays are emitted from the sterilization unit 300, the photocatalytic filter may sterilize the air in response to the UV rays.

In addition, the filter module 200 may be disposed between the sterilization unit 300 and the fan 400 based on a flow of air.

FIG. 11 is a front view illustrating the filter module disposed in the vehicle sterilizing apparatus according to the first embodiment, and FIG. 12 is an exploded perspective view illustrating the filter module disposed in the vehicle sterilizing apparatus according to the first embodiment.

Referring to FIGS. 11 and 12, the filter module 200 according to the first embodiment may include the filter bracket 210, the filter 220 disposed on the filter bracket 210, and a support member 230 which fixes the filter to the filter bracket 210. In this case, the support member 230 may be referred to as a first support member.

The filter bracket 210 may support the filter 220.

In addition, the filter bracket 210 may include a plate portion 211, a wall portion 212 extending downward from the plate portion 211, and a guide protrusion 213 formed to protrude from a side surface of the wall portion 212. In this case, the plate portion 211, the wall portion 212, and the guide protrusion 213 may be integrally formed to minimize an assembly tolerance which may be generated when the filter module 200 is assembled to the housing 100.

The plate portion 211 may be formed in a plate shape. In addition, the plate portion 211 may be disposed between the inlet port 110 and the outlet port 120. In this case, an upper surface of the plate portion 211 may be coplanar with the inlet port 110 and the outlet port 120. Accordingly, the plate portion 211 may support the cover C. In this case, an example in which the upper surface of the plate portion 211 is disposed to be coplanar with the inlet port 110 and the outlet port 120 is illustrated, but the present disclosure is not limited thereto.

The wall portion 212 may be formed in a quadrangular frame shape in which a hole is formed at a center thereof. Accordingly, the filter 220 may be disposed in the hole.

The guide protrusion 213 may guide an arrangement of the filter module 200 coupled to the housing 100.

The guide protrusion 213 may be formed to protrude from the side surface of the wall portion 212 in the width direction. In this case, an end portion of the guide protrusion 213 may be formed as a curved surface.

In addition, the guide protrusion 213 may be formed as a plurality of guide protrusions 213. In this case, the guide protrusion 213 disposed at a lowermost end may be disposed to have a predetermined difference in height when compared to a lower surface 212a of the wall portion 212. That is, the guide protrusion 213 disposed at the lowermost end may be spaced apart from the lower surface 212a. Accordingly, a predetermined space SP may be formed under the guide protrusion 213 disposed at the lowermost end, and the wire W may be disposed in the space SP.

That is, the filter module 200 is disposed between the sterilization unit 300 and the fan 400 based on a flow of air, and the space SP is needed to electrically connect the control unit 500 and the fan 400 using the wire W. Accordingly, the space SP may be used as a path through which the wire W bypasses without being interfered with by the filter module 200. Accordingly, the wire W may electrically connect the fan 400 and the control unit 500 using the space SP.

The filter 220 may be a photocatalytic filter which reacts to UV rays. In this case, the filter 220 may be formed in a form in which ceramic silica ($SiO_2$), which is a base material, is coated with titanium dioxide ($TiO_2$) which is a photocatalyst.

The first support member 230 may be coupled to the wall portion 212 using a fastening member such as a bolt. Accordingly, the first support member 230 may fix the filter 220 disposed on the wall portion 212.

The first support member 230 may be formed in a bar shape. Accordingly, the first support member 230 is advantageous in securing a space when compared to a second support member 230a which will be described below.

The sterilization unit 300 may emit UV rays to the filter 220 to facilitate a sterilizing effect of the filter 220.

The sterilization unit 300 may be inserted into and installed in the second guide 150.

FIG. 13 is a perspective view illustrating the sterilization unit disposed in the vehicle sterilizing apparatus according to the first embodiment.

Referring to FIG. 13, the sterilization unit 300 may include a first substrate 310 and one or more light sources 320 mounted on the first substrate 310.

The first substrate 310 may be positioned at a preset position using the second guide 150.

In addition, the first substrate 310 may be electrically connected to the control unit 500 by the wire W.

The light source 320 may emit UV rays toward the filter 220 to activate sterilization of the filter 220 while sterilizing air. For example, the light source 320 may be provided as an UV light emitting diode (LED) capable of emitting UV rays to activate the photocatalyst of the filter 220. In this case, in order to prevent damage such as deformation due to heat of the UV LED, the first substrate 310 may include a metal material. Accordingly, the first substrate 310 may be referred to as a metal printed circuit board (PCB).

In addition, a plurality of light sources 320 may be disposed on the first substrate 310 in order to improve sterilization capability.

The fan 400 is disposed on the flow channel CH and allows air introduced through the inlet port 110 to be discharged through the outlet port 120. In this case, the fan 400 may be referred to as a blower and may be rotated by an actuator (not shown) such as a motor.

As illustrated in FIGS. 5 and 6, the fan 400 may be disposed to be parallel to the filter module 200.

The fan 400 may be disposed as a plurality of fans 400. Accordingly, since the plurality of the fans 400 are individually replaceable, maintenance costs may be reduced.

In addition, since the plurality of the fans 400 are individually controlled by the control unit 500, air suction performance may be adjusted. For example, when a plurality of occupants ride a vehicle, the sterilizing apparatus 1 may drive the plurality of the fans 400 to improve sterilizing and filtering performance. Furthermore, the sterilizing apparatus 1 may adjust a volume of air discharged through the outlet port 120 by driving only some of the plurality of the fans 400.

The control unit 500 may be electrically connected to the sterilization unit 300 and the fan 400 and may control the sterilization unit 300 and the fan 400 to be driven.

Referring to FIG. 6, the control unit 500 may be disposed in a lower portion of the outlet port 120.

FIG. 14 is a perspective view illustrating the control unit disposed in the vehicle sterilizing apparatus according to the first embodiment.

Referring to FIG. 14, the control unit 500 may include a second substrate 510 and a plurality of elements 520 mounted on the second substrate 510.

The second substrate 510 may be electrically connected to the sterilization unit 300, the fan 400, and the like through the wires W. In addition, external power may be applied to the second substrate 510 through a connection device such as a connector.

The second substrate 510 may be disposed to be spaced apart from the first substrate 310 of the sterilization unit 300. In addition, the first substrate 310 and the second substrate 510 may be electrically connected using the wire W.

In addition, the plurality of elements 520 may be disposed on the second substrate 510. Accordingly, the second substrate 510 may be formed to have a size greater than a size of the first substrate 310. In this case, the second substrate 510 may be disposed to be adjacent to the wall surface 122 at the other side in order to minimize interference with an air flow. In this case, the term "adjacent" may mean that the second substrate 510 is disposed as close as possible to the wall surface 122 at the other side at a predetermined distance in consideration of a size of the element 520.

Accordingly, in the sterilizing apparatus 1, since the first substrate 310, on which only the light source 320 is disposed, and the second substrate 510, on which the elements 520, are disposed are disposed separately, the size of the first substrate 310 may be reduced to be smaller than the size of the second substrate 510. That is, the size of the first substrate 310 may be reduced by arranging the plurality of elements 520 on the second substrate 510.

Accordingly, the sterilizing apparatus 1 may minimize the influence of the first substrate 310 on a flow of air.

FIGS. 15 to 17 are views illustrating an assembly process of the vehicle sterilizing apparatus according to the first embodiment.

Hereinafter, the assembly process of the vehicle sterilizing apparatus according to the first embodiment will be described with reference to FIGS. 15 to 17.

FIG. 15 is a view illustrating an arrangement relationship between the lower housing, the sterilization unit, the fan, and the control unit which are disposed in the vehicle sterilizing apparatus according to the first embodiment.

Referring to FIG. 15, the sterilization unit 300, the fan 400, and the control unit 500 may be coupled to an inner portion of the lower housing 100-2 using the plurality of guides formed in the lower housing 100-2.

FIG. 16 is a view illustrating an arrangement relationship between the upper housing and the lower housing which are disposed in the vehicle sterilizing apparatus according to the first embodiment.

Referring to FIG. 16, the upper housing 100-1 may be coupled to an upper portion of the lower housing 100-2 to which the sterilization unit 300, the fan 400, and the control unit 500 are coupled. Accordingly, the housing 100 is formed by coupling the upper housing 100-1 and the lower housing 100-2. In addition, by the coupling, the flow channel CH through which air flows is formed in the housing 100. In addition, the sterilization unit 300, the fan 400, and the control unit 500 are disposed in the flow channel CH.

FIG. 17 is a view illustrating an arrangement relationship between the housing and the filter module which are disposed in the vehicle sterilizing apparatus according to the first embodiment.

Referring to FIG. 17, the filter module 200 may be detachably disposed in the housing 100 through the hole 130 of the housing 100.

FIG. 18 is a view illustrating a duct member disposed in the vehicle sterilizing apparatus according to the first embodiment.

Light emitted from the light source 320 may be reflected by the filter module 200, and light leakage may occur through the outlet port 120. In this case, the "light leakage" may be light leaking through the outlet port 120.

In addition, an occupant detects the light leakage through the hole H of the cover C and thus feels uncomfortable.

Accordingly, the sterilizing apparatus 1 may prevent the light leakage using a duct member 600.

Referring to FIG. 18, the duct member 600 may be disposed on the outlet port 120 to prevent the light leakage. In this case, the duct member 600 may be formed in a tube shape in order to maintain a flow of air discharged through the outlet port 120. Accordingly, the duct member 600 may be disposed between the cover C and the outlet port 120 to allow the hole H of the cover C to communicate with the outlet port 120.

The duct member 600 may also be disposed on the inlet port 110 in order to support the cover C formed in the plate shape.

Second Embodiment

FIG. 19 is a perspective view illustrating a vehicle sterilizing apparatus according to a second embodiment, FIG. 20 is an exploded perspective view illustrating the vehicle sterilizing apparatus according to the second embodiment, FIG. 21 is a cross-sectional view illustrating the vehicle sterilizing apparatus according to the second embodiment, FIG. 22 is a bottom perspective view illustrating an upper housing of the vehicle sterilizing apparatus according to the second embodiment, FIG. 23 is a perspective view illustrating a lower housing of the vehicle sterilizing apparatus according to the second embodiment, FIG. 24 is a plan view illustrating the lower housing of the vehicle sterilizing apparatus according to the second embodiment, and FIG. 25 is a plan view illustrating the lower housing, a sterilization unit, and a fan of the vehicle sterilizing apparatus according to the second embodiment.

In the description of a sterilizing apparatus 1a according to the second embodiment, in the case of the same reference number referring to the same component described when the sterilizing apparatus 1 according to the first embodiment is described, the redundant description thereof will be omitted.

When the sterilizing apparatus 1 according to the first embodiment and the sterilizing apparatus 1a according to the second embodiment are compared with reference to FIGS. 19 and 25, the sterilizing apparatus 1a according to the second embodiment differs in an arrangement relationship between components disposed in a housing. Accordingly, in the sterilizing apparatus 1a according to the second embodiment, a structure of a housing 100a, a structure of a filter module 200a, and the like may differ from those of the sterilizing apparatus 1 according to the first embodiment.

Particularly, the sterilizing apparatus 1a according to the second embodiment differs from the sterilizing apparatus 1 according to the first embodiment in that a sterilization unit 300 is disposed between a filter 220 and fans 400 based on a flow of air in order to prevent a phenomenon in which light leakage occurs through an outlet port 120. In addition, the sterilizing apparatus 1a according to the second embodiment differs from the sterilizing apparatus 1 according to the first embodiment in that a control unit 500 is disposed in an inlet port 110 in consideration of electrical connection of the sterilization unit 300 and the control unit 500. In addition, due to such a difference in layout, the housing 100a and the filter module 200a may be changed structurally.

The sterilizing apparatus 1a according to the second embodiment may include a flow channel CH formed therein to connect the inlet port 110 and the outlet port 120, the housing 100a including a hole 130 formed to communicate with the flow channel CH, the filter module 200a which filters air in the flow channel CH, the sterilization unit 300 which sterilizes the filter 220 of the filter module 200a, the fans 400 which move air introduced through the inlet port 110 to the outlet port 120, and the control unit 500.

In this case, the filter module 200a may be detachably disposed in the housing 100a through the hole 130.

The housing 100a may form an exterior of the sterilizing apparatus 1a. In addition, the housing 100a may be detachably disposed on a crash pad P in consideration of assemblability.

The housing 100a may include the inlet port 110, the outlet port 120, the flow channel CH connecting the inlet port 110 and the outlet port 120, the hole 130 disposed between the inlet port 110 and the outlet port 120, and a plurality of guides which guide an arrangement of the filter module 200a, an arrangement of the sterilization unit 300, an arrangement of the fan 400, an arrangement of the control unit 500, and an arrangement of wires W.

The housing 100a may include a first guide 140 which guides the arrangement of the filter module 200a.

The first guide 140 may be formed as a plurality of first guides 140 to protrude from a bottom surface 101 of the housing 100a. In addition, the first guide 140 may support the filter module 200a.

The housing 100a may include a second guide 150 which guides the arrangement of the sterilization unit 300 and a third guide 160 which guides the arrangement of the fan 400. In this case, the second guide 150 may be disposed between the first guide 140 and the third guide 160 based on a flow of air.

The second guide 150 may include a first protruding portion 151 formed to protrude from the bottom surface 101 of the housing 100a and a first groove 152.

The third guide 160 may be formed to protrude from the bottom surface 101 of the housing 100a. In this case, the third guide 160 may be formed as a plurality of third guides 160 to correspond to the number of the fans 400 and may support the fans 400.

The housing 100a may include a fourth guide 170 which guides the arrangement of the control unit 500. In this case, the fourth guide 170 may include a second protruding portion 171 formed to protrude from the bottom surface 101 of the housing 100a and a second groove 172.

A one side wall surface of the protruding portion 171 may be coplanar with a wall surface 111 at one side constituting the inlet port 110. That is, the one side wall surface of the protruding portion 171 may be disposed to be coplanar with the wall surface 111 at one side constituting the inlet port 110. Accordingly, the fourth guide 170 and the control unit 500 coupled to the fourth guide 170 may minimize the interference with air suctioned through the inlet port 110. In this case, the wall surface 111 may be referred to as a first inlet port surface.

The housing 100 may guide the arrangement of the wire W connected to the control unit 500 using a fifth guide. In this case, the fifth guide may be a guide wall 180 formed to protrude from the bottom surface 101 of the housing 100a. In this case, the guide wall 180 may be formed in a plate shape.

In addition, the guide wall 180 may be disposed to be spaced apart from one inner side surface of the housing 100a at a predetermined distance in a Y direction. As illustrated in FIG. 25, the wire W may bypass the fan 400 through the guide wall 180 and may be connected to the sterilization unit 300. For example, the wire W electrically connecting the control unit 500 and the sterilization unit 300 may bypass an end portion of the fan 400 in a width direction and may be connected to the sterilization unit 300.

Referring to FIGS. 21 and 22, the housing 100a may include an upper housing 100a-1 and a lower housing 100a-2. In this case, in order to distinguish the upper housing 100a-1 and the lower housing 100a-2 from those of the sterilizing apparatus according to the first embodiment, the upper housing 100a-1 may be referred to as a second upper housing, and the lower housing 100a-2 may be referred to as a second lower housing.

The inlet port 110, the outlet port 120, the hole 130, and the first guide 140 may be formed in the upper housing 100a-1.

The first guide 140 to the fourth guide 170 and the guide wall 180 may be formed in the lower housing 100-2.

FIG. 26 is a front view illustrating the filter module disposed in the vehicle sterilizing apparatus according to the second embodiment, and FIG. 27 is an exploded perspective view illustrating the filter module disposed in the vehicle sterilizing apparatus according to the second embodiment.

In the description of the filter module 200a of the vehicle sterilizing apparatus 1a according to the second embodiment with reference to FIGS. 26 and 27, in the case of the same reference number referring to the same component described when the filter module 200 of the sterilizing apparatus 1 according to the first embodiment is described, the redundant description thereof will be omitted.

The filter module 200a may include a filter bracket 210, a filter 220 disposed on the filter bracket 210, and a support member 230a which fixes the filter 220 to the filter bracket 210. In this case, the support member 230a may be referred to as a second support member.

The filter bracket 210 may include a plate portion 211, a wall portion 212 extending downward from the plate portion 211, and a guide protrusion 213 formed to protrude from a side wall of the wall portion 212.

However, the guide protrusion 213 of the filter module 200a differs from that of the filter module 200 of the vehicle sterilizing apparatus 1 according to the first embodiment in that the space SP is not formed.

The second support member 230a may be coupled to the wall portion 212 using a fastening member such as a bolt. Accordingly, the second support member 230a may fix the filter 220 disposed on the wall portion 212.

The second support member 230a may be formed in a frame shape in which a hole 231 is formed at a center thereof. For example, the second support member 230a may be formed in a quadrangular frame shape in which the hole 231 is formed at the center thereof. Accordingly, the second support member 230a is advantageous in terms of assemblability and fixability when compared to the first support member 230.

FIG. 28 is a perspective view illustrating the control unit disposed in the vehicle sterilizing apparatus according to the second embodiment.

Referring to FIG. 28, the control unit 500 may include a second substrate 510 and a plurality of elements 520 mounted on the second substrate 510. In addition, as illustrated in FIG. 25, the second substrate 510 may be disposed to face the fan 400.

The second substrate 510 may be disposed to be spaced apart from a first substrate 310 of the sterilization unit 300. In addition, the first substrate 310 and the second substrate 510 may be electrically connected using the wire W which by passes the fan 400 through the guide wall 180.

In addition, a groove may be concavely formed in the housing 100a in an X direction in consideration of the plurality of elements 520 of the second substrate 510. Accordingly, in the housing 100a, the element 520 may be prevented from interfering with a flow of air using an accommodation space SP1 formed in the groove.

FIGS. 29 to 31 are views illustrating an assembly process of the vehicle sterilizing apparatus according to the second embodiment.

Hereinafter, the assembly process of the vehicle sterilizing apparatus according to the second embodiment will be described with reference to FIGS. 29 to 31.

FIG. 29 is a view illustrating an arrangement relationship between the lower housing, the sterilization unit, the fan, and the control unit which are disposed in the vehicle sterilizing apparatus according to the second embodiment.

Referring to FIG. 29, the sterilization unit 300, the fan 400, and the control unit 500 may be coupled to an inner portion of the lower housing 100a-2 using the plurality of guides formed in the lower housing 100a-2.

FIG. 30 is a view illustrating an arrangement relationship between the upper housing and the lower housing which are disposed in the vehicle sterilizing apparatus according to the second embodiment.

Referring to FIG. 30, the upper housing 100a-1 may be coupled to an upper portion of the lower housing 100a-2 to which the sterilization unit 300, the fan 400, and the control unit 500 are coupled. Accordingly, the housing 100a is formed by coupling the upper housing 100a-1 and the lower housing 100a-2. In addition, by the coupling, the flow channel CH through which air flows is formed in the housing 100a. In addition, the sterilization unit 300, the fan 400, and the control unit 500 are disposed in the flow channel CH.

FIG. 31 is a view illustrating an arrangement relationship between the housing and the filter module which are disposed in the vehicle sterilizing apparatus according to the second embodiment.

Referring to FIG. 31, the filter module 200a may be inserted into and installed in the housing 100a through the hole 130 of the housing 100a.

According to the embodiments, a sterilizing apparatus, which sterilizes and filters air in a cockpit module, can be implemented to improve vehicle interior hygiene.

According to the embodiments, the sterilizing apparatus can be detachably installed in the cockpit module in addition to a conventional air conditioner and may be disposed under a speaker cover. Accordingly, a degree of design freedom of the cockpit module can be improved according to the embodiments.

According to the embodiments, the marketability of a vehicle can be improved by improving the convenience of replacing the filter module.

Various useful advantages and effects of the embodiments are not limited to the above-described contents and may be more easily understood in the above-described detailed specific descriptions of the embodiments of the present disclosure.

While the present disclosure has been described above with reference to the exemplary embodiments, it may be understood by those skilled in the art that various modifications and changes of the present disclosure may be made within a range without departing from the spirit and scope of the present disclosure defined by the appended claims. In addition, it should be interpreted that differences related to modifications and changes fall within the scope of the present disclosure defined by the appended claims.

What is claimed is:

1. A sterilizing apparatus comprising:
a housing including an inlet port, an outlet port, a flow channel connecting the inlet port and the outlet port, and a hole communicating with the flow channel;
a filter module disposed in the flow channel;
a sterilization unit configured to emit ultraviolet rays toward the filter module; and
a fan configured to move air introduced through the inlet port to the outlet port,
wherein the filter module is inserted into and installed in the housing through the hole,
wherein the filter module includes:
a filter bracket;
a filter disposed on the filter bracket; and
a support member which fixes the filter to the filter bracket,
wherein the sterilization unit is disposed between the filter and the fan, and
wherein the support member has a quadrangular frame shape and includes a hole at a center thereof.

2. A sterilizing apparatus comprising:
a housing including an inlet port, an outlet port, a flow channel connecting the inlet port and the outlet port, and a hole communicating with the flow channel;
a filter module disposed in the flow channel;
a sterilization unit configured to emit ultraviolet rays toward the filter module; and
a fan configured to move air introduced through the inlet port to the outlet port,
wherein the filter module is inserted into and installed in the housing through the hole,
the housing includes a first guide protruding from a bottom surface thereof, and
the first guide is configured to guide an arrangement of the filter module.

3. The sterilizing apparatus of claim 1, wherein the sterilization unit includes:
a first substrate; and
at least one light source which is mounted on the first substrate and configured to emit the ultraviolet rays toward the filter of the filter module,
wherein the first substrate is disposed at a predetermined height due to a second guide protruding from a bottom surface of the housing.

4. The sterilizing apparatus of claim 3, wherein the first substrate includes a metal material.

5. The sterilizing apparatus of claim 3, further comprising a control unit electrically connected to the sterilization unit and the fan,
wherein a second substrate of the control unit is disposed in a lower portion of the inlet port.

6. The sterilizing apparatus of claim 3, further comprising a control unit electrically connected to the sterilization unit and the fan,
wherein:
a guide coupled to the control unit includes a protruding portion and a groove, and
one side wall surface of the protruding portion is coplanar with one side wall surface constituting the inlet port.

7. The sterilizing apparatus of claim 5, wherein:
the second substrate on which a plurality of elements are disposed is disposed to be spaced apart from the first substrate, and
a size of the second substrate is greater than a size of the first substrate.

8. The sterilizing apparatus of claim 5, wherein:
the fan disposed to face the second substrate is disposed as a plurality of fans in the housing, and
the control unit is configured to individually control the plurality of the fans.

9. The sterilizing apparatus of claim 5, wherein:
the second substrate is electrically connected to the sterilization unit and the fan by a wire, and
the housing includes a guide wall so that the wire bypasses the fan and is connected to the sterilization unit.

10. The sterilizing apparatus of claim 1, wherein the filter includes a photocatalytic filter which reacts to the ultraviolet rays.

11. The sterilizing apparatus of claim 1, further comprising a cover disposed to cover the inlet port and the outlet port,
wherein:
the cover includes a hole disposed to face the inlet port and the outlet port, and
one region of the cover is disposed to overlap a speaker.

12. A cockpit module comprising;
a crash pad;
a sterilizing apparatus detachably disposed on the crash pad;
a speaker disposed on the crash pad; and
a cover disposed to cover the speaker,
wherein the cover includes a hole disposed to face an inlet port and an outlet port of the sterilizing apparatus.

13. The cockpit module of claim 12, wherein the sterilizing apparatus includes:
a housing including the inlet port, the outlet port, a flow channel connecting the inlet port and the outlet port, and a hole communicating with the flow channel;
a filter module disposed in the flow channel;
a sterilization unit configured to emit ultraviolet rays toward the filter module; and
a fan configured to move air introduced through the inlet port to the outlet port,
wherein the filter module is inserted into and installed in the housing through the hole.

14. The cockpit module of claim 13, wherein the filter module includes:
a filter bracket;
a filter disposed on the filter bracket; and
a support member which fixes the filter to the filter bracket,
wherein the sterilization unit is disposed between the filter and the fan.

15. The cockpit module of claim 14, further comprising a control unit electrically connected to the sterilization unit and the fan,
wherein a substrate of the control unit is disposed in a lower portion of the inlet port.

16. The cockpit module of claim 12, wherein, when the cover is removed, a filter module disposed in the sterilizing apparatus is exposed.

* * * * *